(12) United States Patent
Gao et al.

(10) Patent No.: US 7,923,550 B2
(45) Date of Patent: Apr. 12, 2011

(54) REAGENT COMPOUNDS AND METHODS OF MAKING AND USING THE SAME

(76) Inventors: Xiaolian Gao, Houston, TX (US); Peilin Yu, Houston, TX (US)

( * ) Notice: Subject to any disclaimer, the term of this patent is extended or adjusted under 35 U.S.C. 154(b) by 1301 days.

(21) Appl. No.: 10/553,328

(22) PCT Filed: Apr. 14, 2004

(86) PCT No.: PCT/US2004/011489
§ 371 (c)(1),
(2), (4) Date: Oct. 14, 2005

(87) PCT Pub. No.: WO2005/000859
PCT Pub. Date: Jan. 6, 2005

(65) Prior Publication Data
US 2007/0060536 A1      Mar. 15, 2007

Related U.S. Application Data
(60) Provisional application No. 60/462,753, filed on Apr. 14, 2003.

(51) Int. Cl.
*C07H 21/00* (2006.01)
(52) U.S. Cl. .................. 536/25.3; 536/25.33; 536/25.34; 568/8
(58) Field of Classification Search .................. None
See application file for complete search history.

(56) References Cited

U.S. PATENT DOCUMENTS

| | | | |
|---|---|---|---|
| 5,843,655 | A | 12/1998 | McGall |
| 6,107,479 | A | 8/2000 | Natt et al. |
| 2003/0227895 | A1 | 12/2003 | Strutt et al. |
| 2005/0169233 | A1 | 8/2005 | Kandala et al. |
| 2005/0186966 | A1 | 8/2005 | Belcea |
| 2006/0029009 | A1 | 2/2006 | Alapuranen et al. |
| 2006/0029010 | A1 | 2/2006 | Belcea |

OTHER PUBLICATIONS

Durand et al. Nucleic Acids Research (1990), vol. 18, pp. 6353-6359.*
Wasserman, S.R., et al. Structure and reactivity of alkylsiloxane monolayers formed by reaction of alkytrichlorosilanes on silicon substrates. *Langmuir*, 5, (1989) 1074-1087.
Balachander, N. et al. Monolayer Transformation by Nucleophilic Substitution: Applications to the Creation of New Monolayer Assemblies. *Langmuir*, 6, (1990) 1621-1627.
Petri, D.F.S., et al. An improved method for the assembly of amino-terminated monolayers on $SiO_2$ and the vapor deposition of gold layers. *Langmuir*, 15, (1999) 4520-4523.
Ingall, M.D.K., et al. Surface functionalization and imaging using monolyers and surface-grafted polymer layers. *J. Am. Chem. Soc.*, 121, (1999) 3607-3613.
Katzhendler, J., et al. The effect of spacer, linkage and solid support on the synthesis of oligonucleotides. *Tetrahedron*, 45, (1989) 2777-2792.

Temsamani, J., et al. Sequence identity of the n -1 product of a synthetic oligonucleotide. *Nucleic Acids Res.*, 23, (1995) 1841-1844.
Fearon, K.L., et al. Investigation of the 'n -1' impurity in phosphorothioate oligodeoxynucleotides synthesized by the solid-phase ~-cyanoethyl phosphoramidite method using stepwise sulfurization. *Nucleic Acids Res.*, 23, (1995) 2754-2761.
Iyer, R.P., et al. Improved procedure for the reduction ofN-I content in synthetic oligonucleotides. *Nucl. Nucl.*, 14, (1995) 1349-1357.
Maskos, U. et al. Oligonucleotide hybridization on glass supports: a novel linker for oligonucleotide synthesis and hybridization of oligonucleotides in situ. *Nucleic Acids Res.*, 20, (1992) 1679-1684.
Gray, D.E., et al. Ellipsometric and interferometric characterization of DNA probes immobilized on a combinatorial array. *Langmuir*, 13, (1997) 2833-2842.
Shchepinov, M.S., et al. Steric factors influencing hybridization of nucleic acids to oligonucleotide arrays. *Nucleic Acids Res.*, 25, (1997) 1155-1161.

(Continued)

*Primary Examiner* — Patrick T Lewis
(74) *Attorney, Agent, or Firm* — G Kenneth Smith

(57) ABSTRACT

The present invention describes novel compounds and methods for capping reactive groups on support and during multistep synthesis. These new capping reagents are also useful for high quality synthesis on solid supports and surfaces used as microarrays, biosensors, or in general as biochips. The compounds are also useful for controlling surface density of reactive groups on a support. The compounds may also be used to modify the hydrophilic/hydrophobic characteristics of a surface or a molecule. The compounds have functional utility in various applications in the fields of genomics, proteomics, diagnostics and medicine.

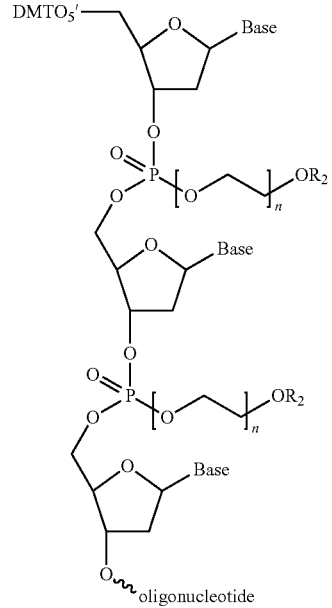

[12]

$R_2 = CH_3$, alkyl, phenyl, $CONH_2$
n = 1–20

3 Claims, 17 Drawing Sheets

OTHER PUBLICATIONS

Guo, Z., et al. Direct fluorescence analysis of genetic polymorphisms by hybridization with oligonucleotide arrays on glass supports. *Nucleic Acids Res.*, 22, (1994) 5456-5465.

Pirrung, M.C. et al. Comparison of methods for photochemical phosphoramidite-based DNA synthesis. *J. Org. Chem.*, 60, (1995) 6270-6276.

Pirrung, M.C. and Fallon, L. Proofing of photolithographic DNA synthesis with 3',5'-dimethoxybenzoinyloxycarbonyl-protected deoxynucleoside phosphoramidites. *J. Org. Chem*, 63, (1998) 241-246.

Pease, A.C., et al. Light-generated oligonucleotide arrays for rapid DNA sequence analysis. *Proc. Natl Acad. Sci. USA*, 91, (1994) 5022-5026.

McGall, G.H., et al. Light-directed synthesis of high-density oligonucleotide arrays using semiconductor photoresists. *Proc. Natl Acad. Sci. USA*, 93, (1996) 13555-13560.

Beier, M. et al. Versatile derivatization of solid support media for covalent bonding on DNA-microchips. *Nucleic Acids Res.*, 27, (1999) 1970-1977.

Yu, D., et al. Diethoxy N, N-diisopropylphosphoramidite as an improved capping reagent in the synthesis of oligonucleotides using phosphoramidite chemistry. *Tetrahedron Letters* 35, (1994) 8565-8568.

Leproust, E., et al. Characterization of oligodeoxyribonucleotide synthesis on glass plates. *Nucleic Acids Res.*, 29, (2001) 2171-2180.

Eckstein, F. (ed.) Oligonucleotides and Analogues, A Practical Approach. IRL Press, Oxford, UK, (1991) 109-135.

Fields, G.B. (ed.) Methods in Enzymology. Academic Press, New York, USA, 289, (2001) Academic Press, New York, USA.

Sears et al. Toward Automated Synthesis of Oligosaccharides and Glycoproteins. Science 291, (2001) 2344-2350, American Association for the Advancement of Science, Washington, D.C. USA.

Harris, J.M. et al. (ed.), Poly(Ethylene Glycol) ACS Symposium Series No. 680 (1997) American Chemical Society, Washington, D.C. USA.

Arakawa, T. et al. Mechanism of Poly(ethylene glycol) Interaction with Proteins, Biochemistry 24, (1985) 6756-6762, American Chemical Society, Washington, D.C., USA.

Zhu, X-Y., et al. Grafting of High-Density Poly(ethylene glycol) Monolayers on Si(111), *Langmuir* 17 (2001) 7798-7803, American Chemical Society, Washington, D.C., USA.

Knoll, E. et al., Unimolecular Beacons for the Detection of DNA-Binding Proteins. *Anal. Chem.* (2004) 76, 1156-1164, American Chemical Society, Washington, D.C., USA.

Choi, Y.H., et al. Polyethylene glycol-grafted poly-L-lysine as polymeric gene carrier, J. Control Release 54, (1998) 39-48, Elsevier Science Publishers, London, UK.

* cited by examiner $R_1 = CH_2CH_2CN, CH_3$
$R_2 = CH_3$, alkyl, phenyl, $CONH_2$
$n = 1 - 20$
$X = NH, S$

[6]

$R_2$, $R_3$ = $CH_3$, alkyl, phenyl, $CONH_2$
i, j = 1 – 20

[13]  = $(N-EG_n)_i$

[14] $(N-EG_n)_i$ – oligonucleotide – $(N-EG_n)_j$ $R_2 = CH_3$, alkyl, phenyl, $CONH_2$, n = 1 – 20; i,j = 1  20
EG = $CH_2CH_2O$, $N_1$, $N_2$, ... $N_i$ are nucleotide residues

REAGENT COMPOUNDS AND METHODS OF MAKING AND USING THE SAME

CROSS-REFERENCE TO RELATED APPLICATION

The present application claims priority under Title 35, United States Code, §119(e)(1) of U.S. Prov. Pat. App. Ser. No. 60/462,753, filed Apr. 14, 2003.

STATEMENT REGARDING FEDERALLY SPONSORED RESEARCH OR DEVELOPMENT

The present invention was developed in part with funds from a grant from The Defense Advanced Research Projects Agency, Grant Number DAAD05-02-C-0038.

BACKGROUND OF THE INVENTION

1. Field of the Invention

The present invention relates to the general fields of biopolymer synthesis and reactions on surfaces of solid or soluble polymers, glass, gold, silica, metal oxide, or other suitable materials (support). This invention particularly provides for chemical compounds to be used as capping agents for the termination of reactive groups on a support and the termination of reactive groups on the first layer of moieties from surface, chain, and/or intermediate sequences of a multiple step synthesis.

2. Description of the Background Art

Biopolymer synthesis on a support has been widely adopted for large-scale combinatorial synthesis, especially for oligonucleotides (Beaton, G. et al., *Oligonucleotides and their Analogues, A Practical Approach*, IRL Press, Oxford, UK, pp. 109-135 (1991)), peptides (Solid-phase peptide synthesis, *Meth. Enzymol.*, Vol. 289, Academic Press: New York (1997)), and carbohydrates (Sears, P. et al., Toward Automated Synthesis of Oligosaccharides and Glycoproteins, *Science* 2350 (2001)). In these syntheses, it is critical high fidelity of the growing chain is achieved with controlled density on solid surfaces. (Maskos, U. et al., *Nucleic Acids Res.*, 20, 1679-1684 (1992); Shchepinov, M. S. et al., *Nucleic Acids Res.*, 25, 1155-1161 (1997); Leproust, E. et al., *Nucleic Acids Res.* 29, 2171-2180 (2001)). High fidelity synthesis requires high yield reactions and the subsequent capping (termination) of the reactive groups so that the reactive groups do not further react until synthesis is complete or the desired deprotection is achieved in a specific reaction step. The controlled density of the molecules synthesized on a support requires a means for placing a certain number of reactive groups on the support regardless of the number of the reactive groups on the original surface. In some cases, a capping reaction using a capping agent is necessary after the reaction to prevent the capping reagent from reacting concomitantly. This becomes more important in synthesis where a monolayer of surface molecules are made.

A common platform for micro-chemical and biological experiments is planar or microscopically planar surfaces. Among these, glass plates (e.g. microscope slides, which are borosilicate glass) or beads are readily available, easy to handle and commonly used. The solid surfaces often used are silicon oxide ($Si/SiO_2$) based, polymeric, or nitrocellulose membrane types. These surface groups do not have ordered structures like those derivatized on $Si/SiO_2$ crystalline silicon surfaces processed in the clean room environments of the semiconductor and micro-electronics industries. In the last few years chemical reactions on glass plate surfaces have been extensively investigated in an effort to understand and optimize synthesis and binding assays on these surfaces.

In addition to factors that affect conventional reactions, such as concentrations and stoichiometric ratios of reagents, specific concerns relate to micro-scale reactions on solid surfaces. These include, for example, the reactivity of surface functional groups, accessibility of the reactants bound to a surface, effective concentration or density of surface molecules and surface microstructures. For oligonucleotide syntheses, earlier studies addressed questions related to bulk solid support materials, such as failure sequences (n–1 sequences where n is the length of the desired sequence) on controlled porous glass (CPG). (Fearon, K. L. et al., *Nucleic Acids Res.*, 23, 2754-2761 (1995); Temsamani, J. et al., *Nucleic Acids Res.*, 23, 1841-1844 (1995); Iyer, R. P. et al., *Nucleic Acid Res.*, 14, 1349-1357 (1995)). The effects of surface functional groups, pore size, chemical properties of linker molecules and linker chain length on synthesis were examined using HPLC and other conventional analytical chemical methods. (Katzhendler, J. et al., *Tetrahedron*, 45, 2777-2792 (1989)). These studies led to the development of highly homogeneous porous glass and synthetic solid support materials containing linkers with desirable chain lengths (e.g. oligoethylene glycosyl linker) or acid/base stable chemical bonds (e.g. ether and amide linkages). In comparison to these bulk syntheses, oligonucleotide syntheses on glass plate surfaces are on the picomolar scale (0.1-1 $pmol/mm^2$). Each spot (micro square) of a microarray of oligonucleotides contains a femtomole or less of material. These micro-quantities of material prevent reactions from being monitored using conventional methods, such as HPLC or UV. In the literature, monitoring of coupling reactions between a nucleotide phosphoramidite (monomer) and the terminal OH group of the immobilized linkers or oligonucleotides were accomplished using fluorescence (FR) measurements. (Leproust, E. et al., *Nucleic Acids Res.*, 29, 2171-2180 (2001); LeProust, E. et al., *J. Comb. Chem.*, 2, 349-354 (2000)). Usually fluorescein phosphoramidites are reacted with the surface terminal OH groups to form fluorescein-terminated oligonucleotides. The intensities of fluorescence emission (FRE) measured following each coupling step are considered proportional to the yields of the coupling reactions. The step-wise yields and the purity of the oligonucleotides synthesized are calculated from these FRE measurements. Using this approach, the efficiency of parallel oligonucleotide synthesis using photolithography and photolabile protection groups is reported to be in the range 82-97%. (Pirrung, M. C. et al., *J. Org. Chem.*, 60, 6270-6276 (1995); McGall, G. H. et al., *J. Am. Chem Soc.*, 119, 5081-5090 (1997); Beier, M. et al., *Nucleic Acids Res.*, 27, 1970-1977 (1999)).

A major cause of lower fidelity synthesis on glass plates is due to the particularly inefficient reactions of the various reagents with the functional groups close to glass plate surfaces. A conventional capping reagent, such as acetic anhydride (Glen Research, Sterling, Va.), for oligonucleotide synthesis especially gives low reaction yields when the reaction sites are close to the surface. Thus, unreacted and uncapped functional groups subsequently react with the nucleophosphoramidites, and the capping and coupling reaction cycles are repeated. The capped sequences are failure sequences which are shorter than full length sequences with the missing residues being at the end closest to the surface. The uncapped and subsequently reacted sequences are also shorter than the full length sequence but they are truncated at the end attached to the surface; these sequences contain deletions of certain residues at the step where coupling and capping failed as shown in FIG. 1.

There are additional problems due the presence of reactive groups on support, such as OH, $NH_2$, or $CO_2H$ groups. The affinity of these groups to proteins, nucleic acids, and other molecules in biological samples causes non-specific adhering and interference with measuring or detecting the specific binding of these biomolecules to their substrate molecules. Non-specific adhering in the binding assays is the origin of high background signal reading, such as fluorescence intensities. This reduces the sensitivity and dynamic range of the devices used for such analyses. It is therefore necessary to cap these reactive groups on the surface of support to reduce non-specific adhering of the various molecules.

One family of polyether molecules has been extensively studied and applied to fields such as industrial processing materials, drug delivery formulation reagents, surface materials, synthesis supports, separation supports, peptide/protein modifiers, and as gradients of the various biomaterials. (Poly (Ethylene Glycol): Chemistry and Biological Applications (*Acs Symposium Series*, No 680) by J. Milton Harris (Editor), Samuel Zalipsky (Editor), American Chemical Society Division of Polymer Chemistry, Calif.) American Chemical Society Meeting 1997 San Francisco, Zalipsky Harris). Typical compounds of the ether family of polymers include oligoethylene glycol (OEG) or oligoethylene oxide, polyethylene glycol (PEG) or polyethylene oxide, oligopropylene oxide (OPO), and polypropylene oxide (PPO). Polymers of ethylene glycol (EG) comprise polyether linkages and the repeating unit is —$(OCH_2CH_2)$—. Polymers of propylene oxide (PO) comprise polyether linkages and the repeating unit is —$(OCH_2CH_2CH_2)$—.

PEG molecules (44 Da per monomer unit and a length of ~3.9 Å per repeating unit in an extended conformation) are amphiphilic in nature, i.e., they possess hydrophilic and hydrophobic properties that allow their solubility in aqueous or organic solvents. PEG dissolves in water to form a biphasic solution with PEG on the top layer and structured water molecules surrounding the PEG chain. Historically, PEG, and especially higher molecular weight PET, is known to be a salt-out reagent that causes protein precipitation. (Arakawa T. et al., *Biochemistry*, 24, 6756-6762 (1985)). This property can be favorably used to prepare a protein-repellant surface. Presently, there is a need for non-adhesive surfaces for protein assays. In light of this need, various PEG surfaces, such as PEG grafted silicon surfaces, have been prepared. (Zhu, X.-Y. et al., *Langmuir*, 17, 7798-7803 (2001)).

Shorter PEG molecules or OEG have been used as spacer or tethers in biopolymer conjugates, such as those used in preparation of oligonucleotide-PEG-oligonucleotide conjugates. (Knoll, E. et al., *Anal. Chem.* 76, 1156-1164 (2004)). In these applications, the OEG used has the general structure of X—$(OCH_2CH_2)_n$—Y, where X and Y are reactive groups that can be attached to the molecules to form a conjugate compound and n is the number of repeating units. As an example, in an OEG used as spacer (Glen Research, Sterling, Va.), X is a phosphoramidite, Y is ODMT (DMT is 4,4'-dimethoxytrityl), and n is six. The phosphoramidite reacts with an OH group, such as the 5'-OH of an oligonucleotide, to form an internucleotide phosphate linkage after the oxidation reaction. DMT can then be easily removed to give an OH group which can couple with a nucleophosphoramidite to form internucleotide phosphate linkage after the oxidation reaction. The final product of these reactions has the structure 5'-oligonucleotide-$(OCH_2CH_2)_6$—O-oligonucleotide-3' which is referred to as conjugated oligonucleotides. The compounds on either side of the spacer do not have to be identical or even of the same type of molecule. For instance, a peptide can be tethered with an oligonucleotide to give a peptide-oligonucleotide conjugate; or, an oligonucleotide can be tethered to a surface reactive group to be immobilized on surface.

SUMMARY OF THE INVENTION

The present invention includes compounds of the Formula I and Formula II, methods of making and using such compounds, and products made by such methods, as shown immediately below:

Formula I where $R_1$ is —$CH_2CH_2CN$, —$CH_2CH_3$, —$CH_3$, -phenyl optionally substituted by one or more halogens, or -$[A]_n$-$OR_4$;
$R_2$ is —$CH_2CH_2CN$, —$CH_2CH_3$, —$CH_3$, -phenyl optionally substituted by one or more halogens, or —$[B]_n$—$OR_4$;
$R_3$ is —$CH_3$, —$CH_2CH_3$, or —$CH(CH_3)_2$;
$R_4$ is —$CH_3$, -alkyl, -phenyl, or —$CONH_2$;

A is $(CH_2CH_2O)$, $(CH_2CH_2CH_2O)$,

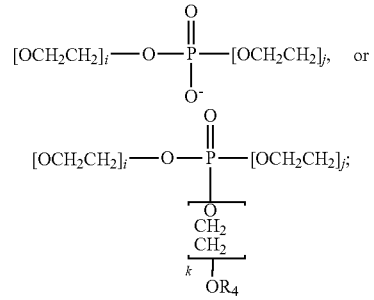

B is $(CH_2CH_2O)$, $(CH_2CH_2CH_2O)$,

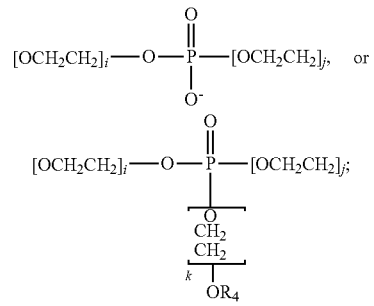

i, j, k, n are 1-20; and
where at least $R_1$ is $[A]_n$-$OR_4$ or $R_2$ is $[B]_n$—$OR_4$ or $R_1$ is $[A]_n$-$OR_4$ and $R_2$ is $[B]_n$—$OR_4$.

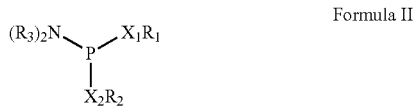

Formula II where $X_1$ is O, NH, or S;
$X_2$ is O, NH, or S;
where at least $X_1$ is NH or S, or $X_2$ is NH or S;

$R_1$ is —$CH_2CH_2CN$, —$CH_2CH_3$, —$CH_3$, -phenyl optionally substituted by one or more halogens, or -$[A]_n$-$OR_4$;
$R_2$ is —$CH_2CH_2CN$, —$CH_2CH_3$, —$CH_3$, -phenyl optionally substituted by one or more halogens, or —$[B]_n$—$OR_4$;
$R_3$ is —$CH_3$, —$CH_2CH_3$, or —$CH(CH_3)_2$;
$R_4$ is —$CH_3$, -alkyl, -phenyl, or —$CONH_2$;

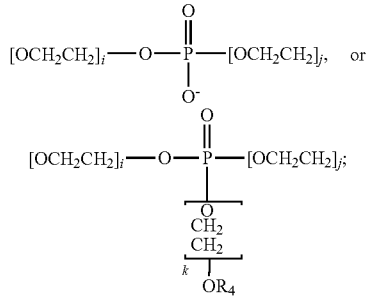

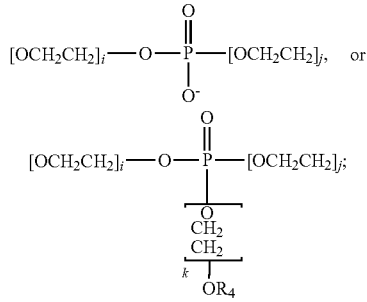

i, j, k, n are 1-20; and
where at least $R_1$ is $[A]_n$-$OR_4$ or $R_2$ is —$[B]_n$—$OR_4$ or $R_1$ is $[A]_n$-$OR_4$ and $R_2$ is $[B]_n$—$OR_4$.

Compounds of the Formula I and Formula II are useful for capping reactive groups such as, but not limited to, OH, $NH_2$, and carboxylate ester. These chemical compounds are also useful for capping failure sequences during oligonucleotide synthesis. The capping reactive groups can be on supports or on surface molecules such as, but not limited to, oligonucleotides. The compounds of the present invention react efficiently to form covalent bonds with the reactive groups to be terminated, making the reactive groups chemically stable in subsequent reaction steps which do not involve the capped groups. Capping using the compounds of the present invention in a multi-step synthesis improves the quality of the final product. In addition, such compounds can modify surface properties through attachment to surface bound molecules, making surfaces non-adhesive to potential proteins, nucleic acids, and biological molecules which come in contact with the surface. The compounds are useful for adjusting the density of surface functional groups by terminating or quantitatively terminating reactive groups. The compounds of the present invention can also be used to modify the hydrophobicity and hydrophilicity properties of the molecules through attachment to the reactive groups of the molecules. One of the useful applications of such modification is to modify the surface properties using the compounds of the present invention through reaction with surface reactive groups. The present invention also includes an oligomeric compound linked to at least one of the compounds of Formula I and Formula II.

BRIEF DESCRIPTION OF FIGURES

For a detailed understanding and better appreciation of the present invention, reference should be made to the following detailed description of the invention, taken in conjunction with the accompanying figures.

DETAILED DESCRIPTION OF THE INVENTION

The present invention is a compound of Formula I as set out below:

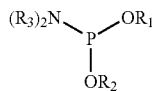

where R$_1$ is —CH$_2$CH$_2$CN, —CH$_2$CH$_3$, —CH3, -phenyl optionally substituted by one or more halogens, or -[A]$_n$-OR$_4$;
R$_2$ is —CH$_2$CH$_2$CN, —CH$_2$CH$_3$, —CH$_3$, -phenyl optionally substituted by one or more halogens, or —[B]$_n$—OR$_4$;
R$_3$ is —CH$_3$, —CH$_2$CH$_3$, or —CH(CH$_3$)$_2$;
R$_4$ is —CH$_3$, -alkyl, -phenyl, or —CONH$_2$;

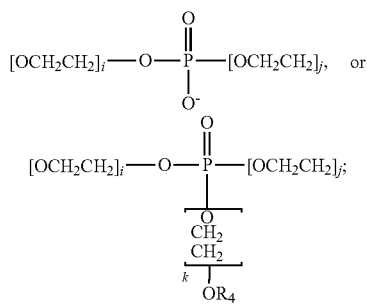

A is (CH$_2$CH$_2$O), (CH$_2$CH$_2$CH$_2$O),

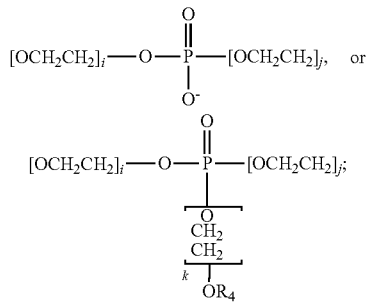

B is (CH$_2$CH$_2$O), (CH$_2$CH$_2$CH$_2$O), i, j, k, n are 1-20; and
where at least R$_1$ is [A]$_n$-OR$_4$ or R$_2$ is [B]$_n$—OR$_4$ or R$_1$ is [A]$_n$-OR$_4$ and R$_2$ is [B]$_n$—OR$_4$.

Figure 2:
FIG. 2 shows examples of phosphoramidites containing a polyethylene glycol substitution chain.
Figure 2:

A phosphoramidite compound of Formula I is shown in FIG. 2 and immediately below:

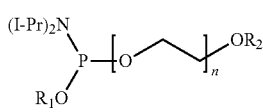

where R$_1$ is —CH$_2$CH$_2$CN, —CH$_2$CH$_3$ or —CH$_3$;
R$_2$ is —CH$_3$, -alkyl, -phenyl, or —CONH$_2$;
I—Pr is isopropyl; and
n is 1 to 20.

Figure 3:
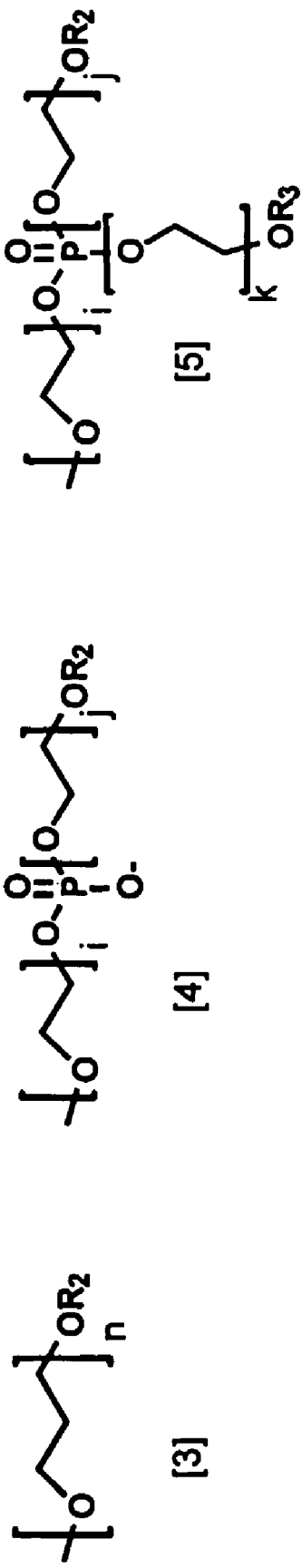
FIG. 3 shows examples of different structures of polyethylene glycol and polypropylene glycol substitution chains in a phosphoramidite.

Another phosphoramidite compound of Formula I, having a polypropylene glycol substitution chain, is shown in FIG. 3 and immediately below:

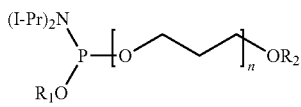

where R$_1$ is —CH$_2$CH$_2$CN or —CH$_3$;
R$_2$ is —CH$_3$, -alkyl, -phenyl, or —CONH$_2$;
I—Pr is isopropyl; and
n is 1 to 20.

Yet another phosphoramidite compound of Formula I, having a polyethylene glycol substitution chain, is shown in FIG. 3 and immediately below:

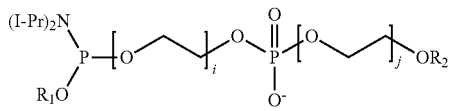

where R$_1$ is —CH$_2$CH$_2$CN or —CH$_3$;
R$_2$ is —CH$_3$, -alkyl, -phenyl, or —CONH$_2$;
I—Pr is isopropyl; and
i and j are 1 to 20.

Yet another phosphoramidite compound of Formula I, having a polyethylene glycol substitution chain, is shown in FIG. 3 and immediately below:

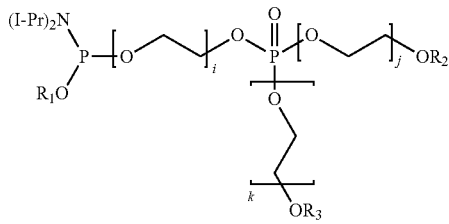

where R$_1$ is —CH$_2$CH$_2$CN or —CH$_3$;
R$_2$ is —CH$_3$, -alkyl, -phenyl, or —CONH$_2$; and
i, j, and k are 1 to 20.

Figure 4:
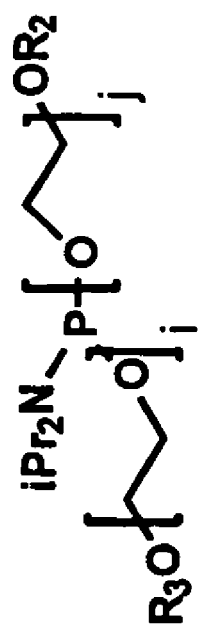
FIG. 4 shows example of phosphoramidite containing dipolyethylene glycol substitution chains.

Yet another phosphoramidite compound of Formula I is shown in FIG. 4 and immediately below:

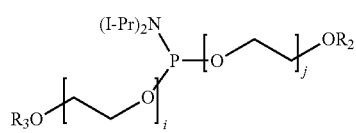

where R$_2$ and R$_3$ are —CH$_3$, -alkyl, or -phenyl;
I—Pr is isopropyl; and
i and j are 1 to 20.

The present invention is also a compound of Formula II as set out below:

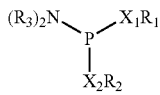

where $X_1$ is O, NH, or S;
$X_2$ is O, NH, or S;
Where at least $X_1$ is NH or S, or $X_2$ is NH or S;
$R_1$ is —$CH_2CH_2CN$, —$CH_2CH_3$, —$CH_3$, -phenyl optionally substituted by one or more halogens, or -$[A]_n$-$OR_4$;
$R_2$ is —$CH_2CH_2CN$, —$CH_2CH_3$, —$CH_3$, -phenyl optionally substituted by one or more halogens, or —$[B]_n$—$OR_4$;
$R_3$ is —$CH_3$, —$CH_2CH_3$, or —$CH(CH_3)_2$;
$R_4$ is $CH_3$, -alkyl, -phenyl, or —$CONH_2$;

A is ($CH_2CH_2O$), ($CH_2CH_2CH_2O$),

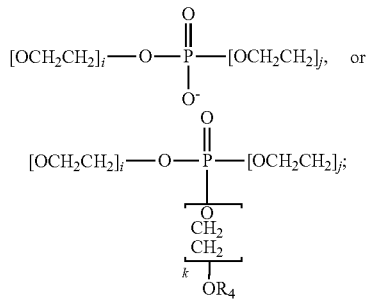

B is ($CH_2CH_2O$), ($CH_2CH_2CH_2O$),

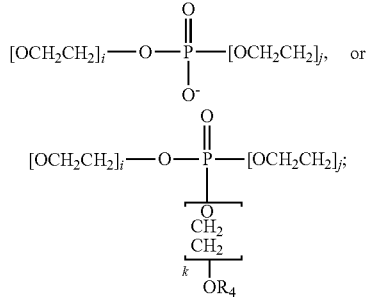

i, j, k, n are 1-20; and
where at least $R_1$ is $[A]_n$-$OR_4$ or $R_2$ is —$[B]_n$—$OR_4$ or $R_1$ is $[A]_n$-$OR_4$ and $R_2$ is $[B]_n$—$OR_4$.

A phosphoramidite compound of Formula II is shown in FIG. 2 and immediately below:

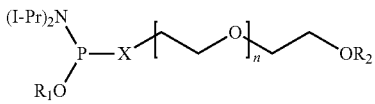

where $R_1$ is —$CH_2CH_2CN$ or —$CH_3$;
$R_2$ is —$CH_3$, -alkyl, -phenyl, or —$CONH_2$;
I—Pr is isopropyl;
n is 1 to 20; and
X is NH or S.

As shown above, the compounds of Formula I and Formula II may include "oligoethylene glycol (OEG)", "polyethylene glycol (PEG)", "polyethylene oxide", "oligoethylene oxide", "oligopropylene oxide (OPO)", polypropylene oxide (PPO)". The compounds of Formula I and Formula II may include combinations of "oligoethylene glycol (OEG)", "polyethylene glycol (PEG)", "polyethylene oxide", "oligoethylene oxide", "oligopropylene oxide (OPO)", polypropylene oxide (PPO)". Polymers of ethylene glycol (EG) comprise polyether linkages and the repeating unit is —($OCH_2CH_2$)—. Polymers of propylene oxide (PO) comprise polyether linkages and the repeating unit is —($OCH_2CH_2CH_2$)—.

The present invention also includes a process for preparing a compound of Formula I:

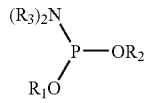

comprising the step of reacting HO—$R_2$ with

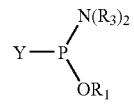

wherein Y is a halogen;
$R_1$ is —$CH_2CH_2CN$, —$CH_2CH_3$, —CH3, -phenyl optionally substituted by one or more halogens, or -$[A]_n$-$OR_4$;
$R_2$ is —$CH_2CH_2CN$, —$CH_2CH_3$, —CH3, -phenyl optionally substituted by one or more halogens, or —$[B]_n$—$OR_4$;
$R_3$ is —$CH_3$, —$CH_2CH_3$, or —$CH(CH_3)_2$;
$R_4$ is —$CH_3$, -alkyl, -phenyl, or —$CONH_2$;

A is ($CH_2CH_2O$), ($CH_2CH_2CH_2O$),

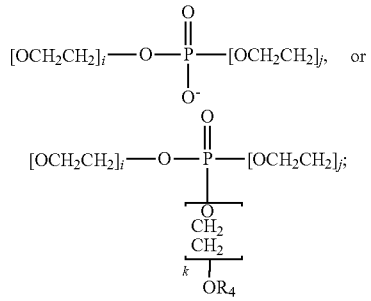

B is ($CH_2CH_2O$), ($CH_2CH_2CH_2O$),

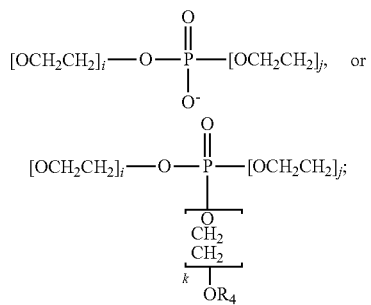

i, j, k, n are 1-20; and
where at least $R_1$ is $[A]_n$-$OR_4$ or $R_2$ is $[B]_n$—$OR_4$ or $R_1$ is $[A]_n$-$OR_4$ and $R_2$ is $[B]_n$—$OR_4$.

A compound of Formula II may be prepared by reacting $R_2$—$X_2H$ with

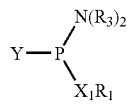

where $X_2$ is O, NH, or S;
$X_1$ is NH or S;
Y is a halogen;
$R_1$ is —$CH_2CH_2CN$, —$CH_2CH_3$, —$CH_3$, -phenyl optionally substituted by one or more halogens, or -$[A]_n$-$OR_4$;
$R_2$ is —$CH_2CH_2CN$, —$CH_2CH_3$, —CH3, -phenyl optionally substituted by one or more halogens, or —$[B]_n$—$OR_4$;
$R_3$ is —$CH_3$, —$CH_2CH_3$, or —$CH(CH_3)_2$;
$R_4$ is —$CH_3$, -alkyl, -phenyl, or —$CONH_2$;

A is ($CH_2CH_2O$), ($CH_2CH_2CH_2O$),

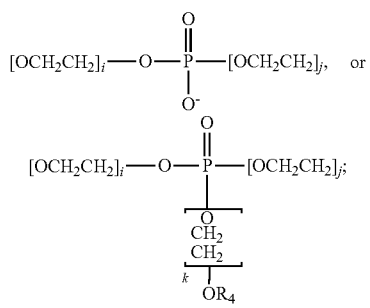

B is ($CH_2CH_2O$), ($CH_2CH_2CH_2O$),

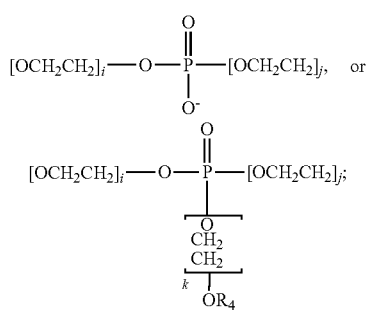

i, j, k, n are 1-20; and
where at least $R_1$ is $[A]_n$-$OR_4$ or $R_2$ is $[B]_n$—$OR_4$ or $R_1$ is $[A]_n$-$OR_4$ and $R_2$ is $[B]_n$—$OR_4$.

The compounds of the Formula I and Formula II and containing the pentavalent phosphate moieties with a P=O functional group are synthesized using a compound of the formula HO—($CH_2CH_2O$)$_n$—X where is a protecting group such as DMT. The compound is reacted with a compound of the Formula I or Formula II followed by oxidation with $I_2/H_2O$/lutidine under the conditions which are well known for making oligonucleotides. After purification of the product, the DMT group is removed under acid conditions which is well known for deprotection of DMT group in oligonucleotide synthesis to give the product of the Formula I and Formula II where A or B is as shown above but not —($CH_2CH_2O$), —($CH_2CH_2CH_2O$).

The present invention is also an oligomer or an oligomeric compound linked to at least one of the compounds of Formula I and Formula II. The combination of the oligomer or oligomeric compound and the compound of Formula I or Formula II is sometimes referred to herein as a chimeric oligonucleotide.

A chimeric oligonucleotide of the subject invention is shown immediately below:

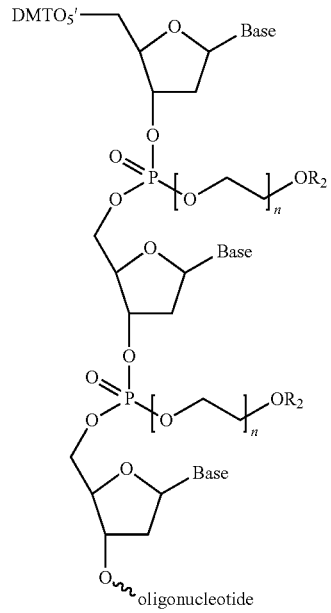

Figure 8:
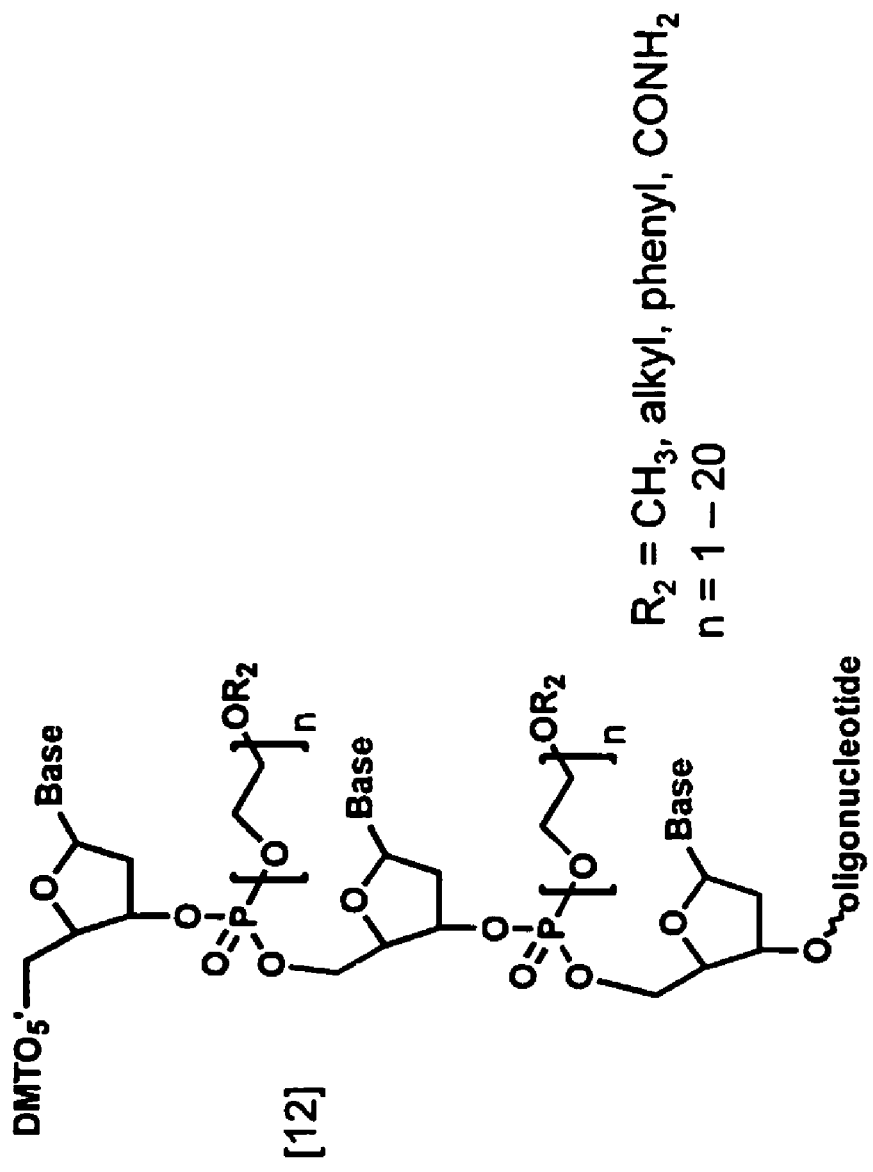
FIG. 8 shows an example of dinucleotide containing polyethylene glycosyl phosphotriester linkage.

This compound is also shown in FIG. 8. An oligomer or an oligomeric compound can be, but is not limited to, a nucleoside, a nucleotide, an oligonucleotide, a growing oligonucleotide chain, a peptide, an amino acid or an oligosaccharide.

Figure 7:
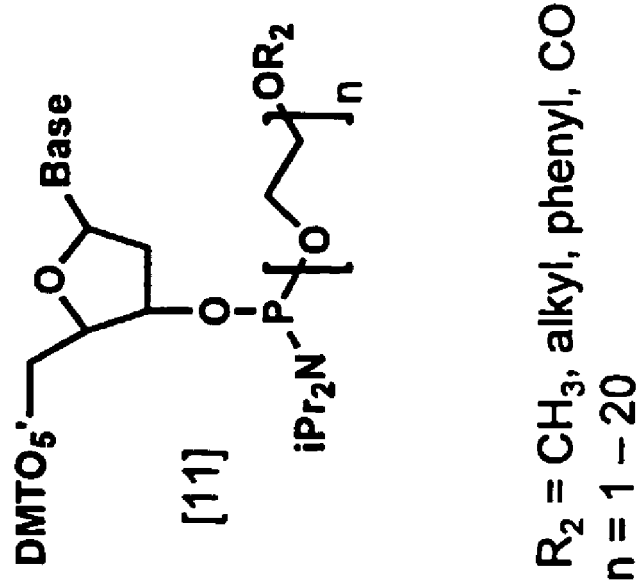
FIG. 7 shows an example of nucleophosphoramidite containing polyethylene glycosyl substitution on phosphorus.

To produce the chimeric oligonucleotide, the phosphorus of the compound of Formula I can react with the 3'-OH group of a nucleoside to form a building block as shown in FIG. 7 and immediately below:

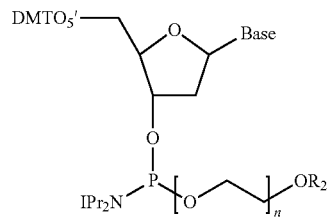

Figure 5:
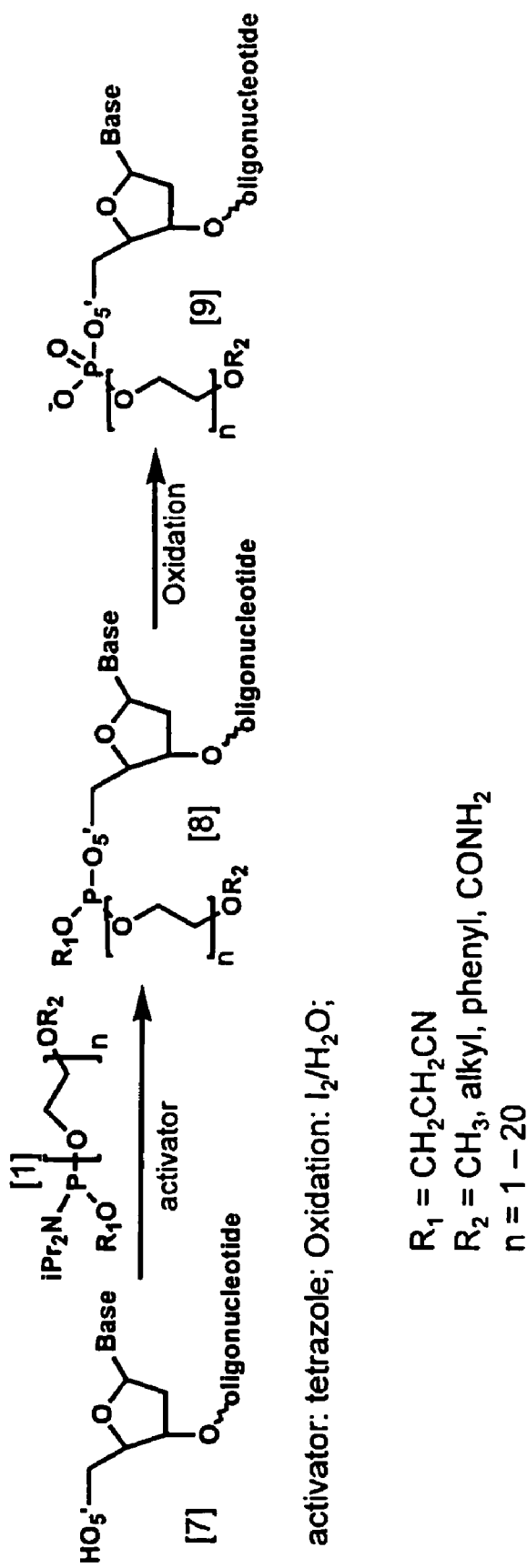
FIG. 5 illustrates a capping reaction involving a capping reagent and terminus 5'-OH of an oligonucleotide.

In addition, the phosphorus compound of Formula I can react with the 5'-OH group as shown in FIG. 5.

Figure 6:
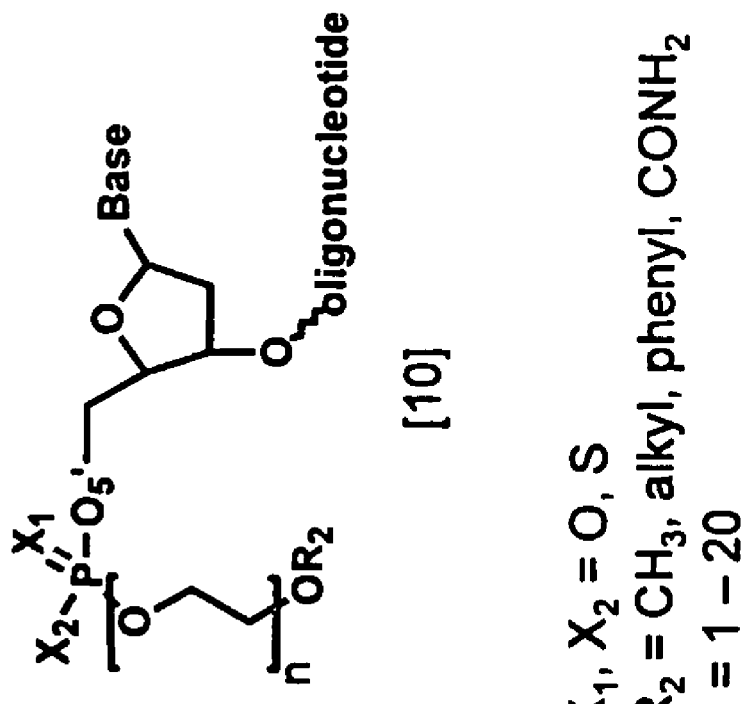
FIG. 6 shows an example of the compound formed after the reaction of capping reagent with 5'-OH of oligonucleotide followed by oxidation ($X_1$, $X_2$=O) or sulfurylation ($X_1$, $X_2$=S).

Alternatively, oxidation may be substituted with sulfurization as shown in FIG. 6 and immediately below:

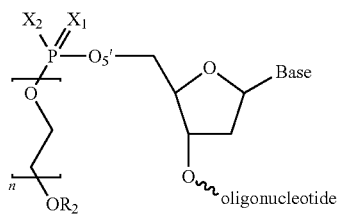

where $X_1$ and $X_2$ are either S or O and where $X_1$ and $X_2$ may not be identical.

Figure 9:
FIG. 9 depicts oligonucleotides containing polyethylene glycosyl phosphotriester linkages.
Figure 9:

Chimeric oligonucleotides may be represented by various forms. For example, grafted PEG-oligonucleotide polymeric conjugates are shown in FIG. 9 and immediately below:

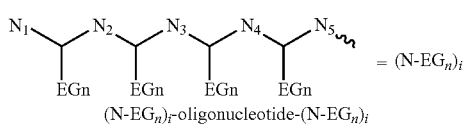

$(N\text{-}EG_n)_i\text{-oligonucleotide-}(N\text{-}EG_n)_i$ wherein N represents a nucleotide unit, $EG_n$ is a PEG chain bonded to a phosphotriester internucleotide linkage (N-EG), and the structure is formed by repeating units of $N\text{-}EG_n$ is $(N\text{-}EGn)_i$ or $(N\text{-}EGn)_j$ which covalently joins to an oligonucleotide to form a grafted PEG-oligonucleotide polymeric conjugate. There is no limit to the length of the oligonucleotide, but it comprises at least one nucleotide residue. Furthermore, the arrangement of the $N\text{-}EG_n$ segment and the oligonucleotide is not limited to what is shown above or in FIG. 9. For example, a grafted PEG-oligonucleotide polymeric conjugate needs only one $N\text{-}EG_n$ segment (but may have additional segments) and one oligonucleotide in any order of arrangement.

An example chimeric oligonucleotide of the subject invention is shown immediately below:

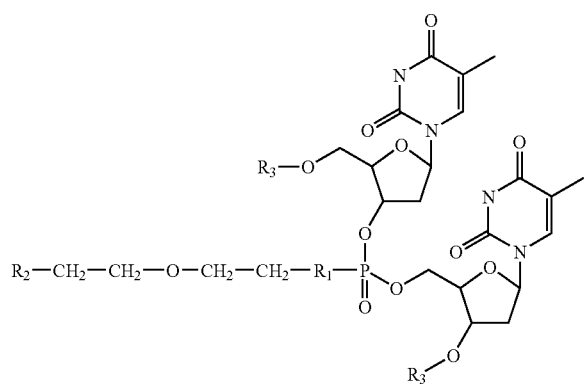

where $R_1$ is O, S, or NH;
$R_2$ is OMe, OEt, Ak, Cy, Cb, Hy, or A;
$R_3$ is OH, Ak, Cy, Cb, or Hy;
A is any atom except H;
Ak is any alkyl chain;
Cy is any cyclic compound;
Cb is any carbocyclic compound; and
Hy is any heterocyclic compound.

Another example chimeric oligonucleotide of the subject invention is shown immediately below:

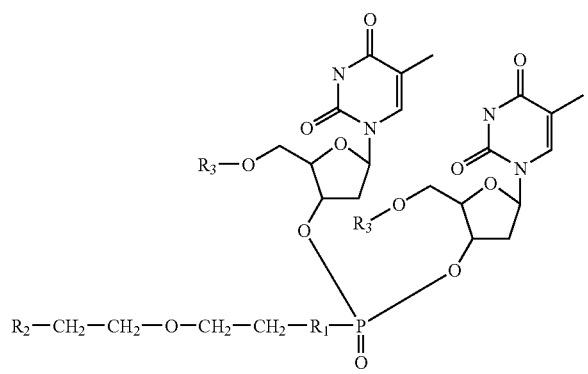

where $R_1$ is O, S, or NH;
$R_2$ is OMe, OEt, Ak, Cy, Cb, Hy, or A;
$R_3$ is OH, Ak, CY, Cb, or Hy;
A is any atom except H;
Ak is any alkyl chain;
Cy is any cyclic compound;
Cb is any carbocyclic compound; and
Hy is any heterocyclic compound.

Yet another example chimeric oligonucleotide of the subject invention is shown immediately below:

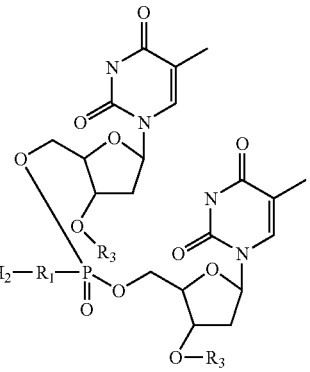

where $R_1$ is O, S, or NH;
$R_2$ is OMe, OEt, Ak, Cy, Cb, Hy, or A;
$R_3$ is OH, Ak, Cy, Cb, or Hy;
A is any atom except H;
Ak is any alkyl chain;
Cy is any cyclic compound;
Cb is any carbocyclic compound; and
Hy is any heterocyclic compound.

DEFINITIONS

To facilitate the understanding of the invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

"3'" means a region or position in a polynucleotide or oligonucleotide related to the 3' position of ribose ring of a nucleotide and downstream from this position in the same polynucleotide or oligonucleotide.

"5'" means a region or position in a polynucleotide or oligonucleotide related to the 5' position of ribose ring of a nucleotide and upstream from this position in the same polynucleotide or oligonucleotide.

A nucleoside is a purine (adenine (A) or guanine (G) or derivative thereof) or pyrimidine (thymine (T), cytosine (C) or uracil (U), or derivative thereof) base bonded to a sugar. The four nucleoside units (or bases) in DNA are called deoxyadenosine, deoxyguanosine, deoxythymidine, and deoxycytidine.

A nucleotide is a phosphate ester of a nucleoside. As used interchangeably herein, the terms "polynucleotide," "oligonucleotide" and "nucleic acid" include single-stranded DNA (ssDNA), double-stranded DNA (dsDNA), single-stranded RNA (ssRNA) and double-stranded RNA (dsRNA), modified oligonucleotides and oligonucleosides, or combinations thereof. The nucleic acid can be linearly or circularly configured, or the oligonucleotide can contain both linear and circular segments. Nucleic acids are polymers of nucleosides joined, e.g., through phosphodiester linkages or alternate linkages, such as phosphorothioate esters. In the context of this invention the term "oligonucleotide" is a chain of one or more nucleotides and can be a polymer or an oligomer of ribonucleic acid or deoxyribonucleic acid. This term may include oligonucleotides composed of naturally-existing nucleobases and sugars as well as oligonucleotides having non-naturally-occurring segments which function similarly. Modified or substituted oligonucleotides may have desirable properties such as, for example, enhanced cellular uptake, enhanced binding to target and increased stability.

An oligomer, otherwise referred to herein as an oligomeric compound, is an oligonucleotide, a peptide or an oligosaccharide or repeating units thereof.

A "support" is a surface of polymers, glass, silica, gold, metal oxide, and/or other suitable materials used for chemical reaction and may be provided in the form of solid or polymers in soluble forms.

"Capping" means to block reactive functional group from further chemical reactions through the attachment of a chemical moiety that is unreactive under the condition that the reactive group would react. The product of capping may be reversible or irreversible under given chemical reaction conditions after at least one reaction step is carried out after the capping reaction.

A "capping reagent" means a compound containing a chemical moiety that can be attached to a reactive group during the capping reaction.

A "failure sequence" is a compound that does not have the structure and/or the sequence of the desired synthesis. An example of a failure sequence is an olignucleotide starting material that failed to undergo reaction with the 5'-protected contacting monomer unit.

A "peptide" is a polymer in which the monomers are amino acids joined together by amide bonds. Peptides are two or more amino acid monomers long. The amino acids may be naturally or non-naturally occurring and may include modifications resulting from phosphorylation, glycosylation, pegylation, lipidization and methylation reactions.

A "block polymer" is a type of chemical moiety covalently linked in an alternating form. There is no limit to the order or how the different chemical moieties are connected or to the length of the different chemical moieties in the block polymer.

"Reactive group" or "reactive functional group" is a functional group that may react with other available functional groups under specified conditions to yield a covalent linkage.

A "growing oligonucleotide chain" is an intermediate product in the synthesis by the sequential addition of nucleotides including, but not limited to, either a 5'- or 3'-protected oligonucleotide chain or a 5' or 3'-protected made by the sequential addition of nucleotides.

Solid-phase oligonucleotide synthesis is a method of oligonucleotide synthesis in which the starting material such as a nucleoside is attached to a solid support. Examples of solid supports include but are not limited to functionalized glass, controlled porous glass (CPG), polystyrene, polyethylene gycol, polymer, polymer resin, grafted polymer, nylon filters, cellulosic filters, resin, membrane, polymer etc.

Solution-phase oligonucleotide synthesis is a method of oligonucleotide synthesis characterized by the use of an anchor group attached to the 5'-end of the growing oligonucleotide that allows a successfully coupled product to be separated from unreacted starting materials.

A "biological chip" or a "biochip" or a "microarray" is a collection of miniaturized test sites arranged on a substrate that permits many tests to be performed at the same time in order to achieve higher throughput and speed. Like a computer chip, which can perform millions of mathematical operations per second, a biochip can perform thousands to millions of biochemical and biological reactions, such as decoding genes quickly. In addition to gene expression profiling and genetic analysis applications, a biochip may be used in toxicological, protein, and biochemical research. Biochips may also be used to rapidly detect chemical agents. A microarray may include an array of DNA or protein samples that can, for example, be hybridized with probes to study patterns of gene expression.

A microfluidic chip means a compound that reacts with reactive group of a reactant compound to form product that has different chemical properties from the reactant compound before its reaction with modifier.

Cyclic means any cycloalkyl, for example, cyclopropane.

Carbocyclic means any compound with a homocyclic ring in which all the ring atoms are carbon, for example, benzene.

Heterocyclic means any compound in which the ring structure is a combination of more than one kind of atom.

A method of synthesizing an oligomer comprising the use of the compounds of Formula I or Formula II is provided. The oligomer can be an oligonucleotide, a peptide or an oligosaccharide or a conjugate molecule comprised of nucleotide, amino acid and/or carbohydrate. In one embodiment of the present invention the oligomer is an oligonucleotide. An oligonucleotide can include any sequence of DNA or RNA having at least one nucleotide residue. There is no limit to the length of the olignucleotide. In another embodiment, the oligonucleotide is a DNA sequence.

A oligomer can be synthesized using procedures well known in the art such as solution-phase method or solid-phase method. For example, a solution-phase method for the synthesis of an oligonucleotide includes an anchor group attached to the 5'-end of the growing oligonucleotide which allows successfully coupled products to be separated from unreacted starting materials. One such solution-phase method is described in the Detailed Description of The Invention of Pieken et al. U.S. Pat. No. 6,262,251, entitled "Method for Solution Phase Synthesis of Oligonucleotides," col. 8, ls. 5-28, which is incorporated herein by reference.

On the other hand, solid-phase methods for synthesizing oligonucleotides employ the use of phosphate triesters or phosphates (Letsinger, S. L. and Lunsford, W. B. 1976. J. Am. Chem. Soc. 98, 3655-3661), or H phosphonate (Garegg, P J. et al. 1985. Chemica Scripta 25, 280-282).

Another solid-phase method utilizes phosphoramidite chemistry (Beaucage, S. L. and Caruthers, M. H. 1981. Tetrahedron Lett. 22, 1859-1862). These methods generally build the oligonucleotide chain as anchored to a solid support through its 3'OH group and coupling 5'-deprotected groups.

Figure 12:
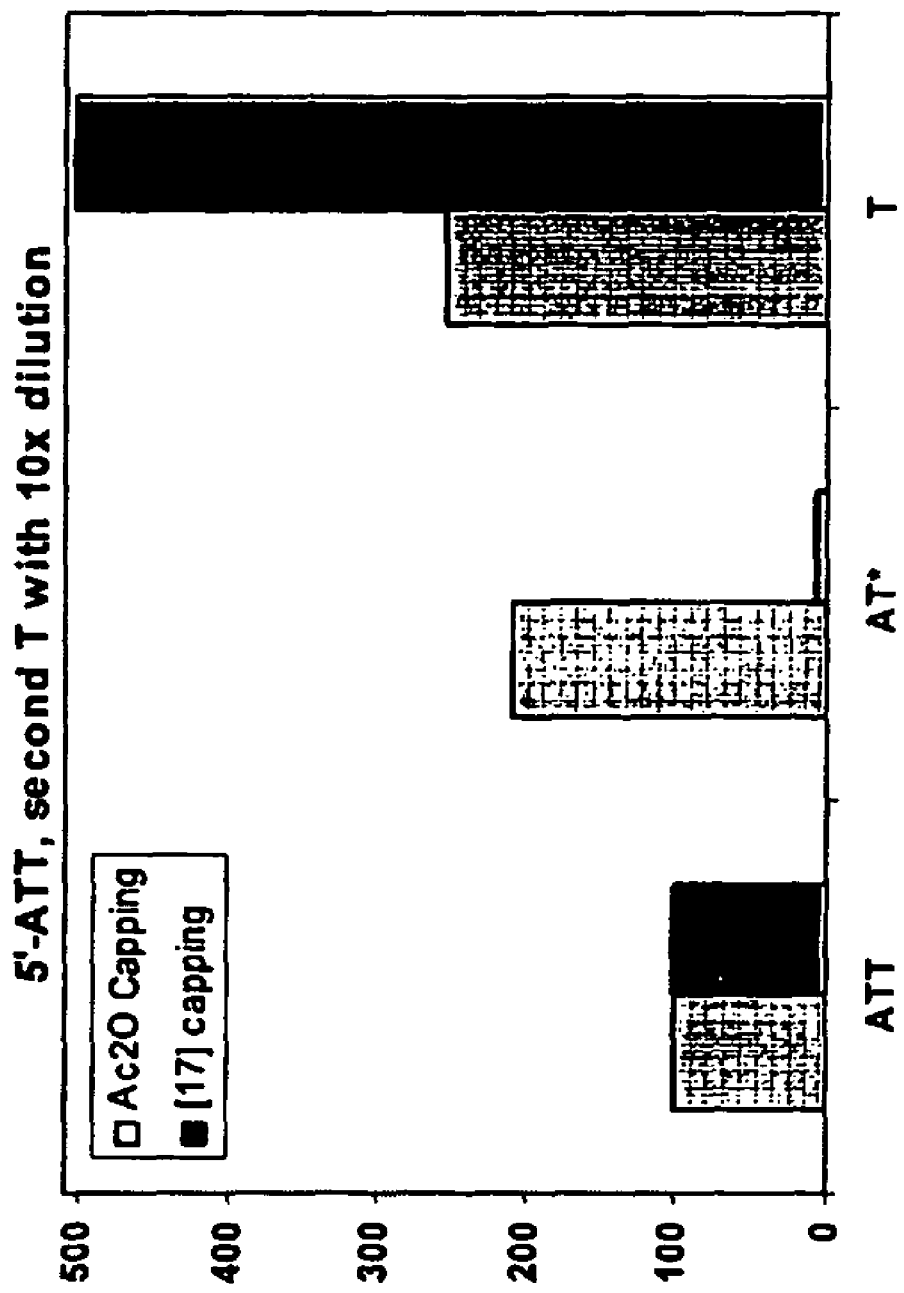
FIG. 12 illustrates the results of capping efficiency measured the height of T (in the reaction of Ac2O capping or capped-T (in the reaction of [17] capping), for synthesis of 5'-ATT. The second step reaction for coupling T used diluted T phosphoramidite (dilution factor=10). [17] denotes diethylene glycol monoethyl ether phosphoramidite.

As shown in FIG. 12, oligonucleotides are synthesized by the solid phase method using phosphoramidite chemistry. Typical solid-phase olignucleotide synthesis involves reiteratively performing four steps: deprotection, coupling, capping and oxidation. In the first step, deprotection, the growing olignonucleotide which is attached to a support via its 3' OH group is 5'-deprotected to provide a reactive group (5'-OH group). In the second step, coupling, the 5'-deprotected oligonucleotide is reacted with the desired nucleotide monomer. Prior to reaction, the nucleotide monomer is first converted to a 5'-protected, 3'-phosphoramidite. The 3'-phosphoramidite group of the nucleotide monomer then reacts with the deprotected 5'-OH group of the growing oligonucleotide to yield the phosphite linkage 5'-OP(OR')O-3'. Not all of the growing oligonucleotides will couple with the provided monomer.

Figure 1:
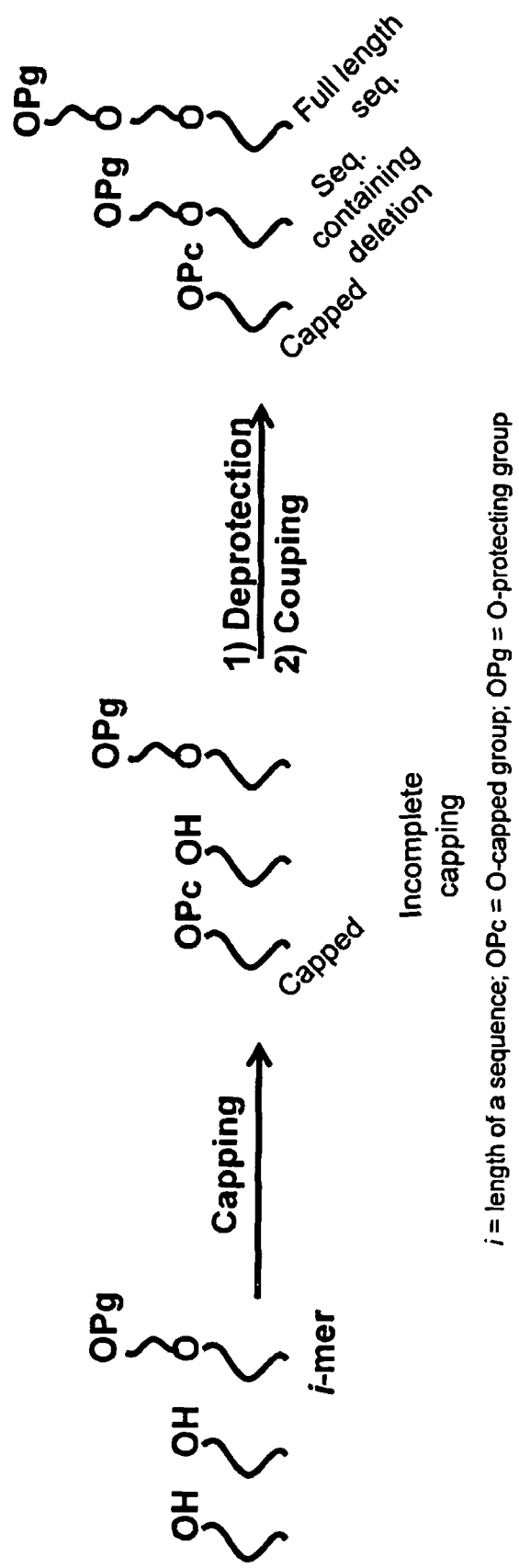
FIG. 1. illustrates the formation of failure and erroneous sequences due to incomplete capping reactions.

Thus, as shown in FIG. 1, those oligonucleotides which are not elongated are called "failure sequences" because they are incomplete oligonucleotides and must be eliminated as templates from further synthesis. This is achieved by the third step, capping, in which all of the remaining —OH groups (i.e., unreacted 5'-OH groups) are capped using the compounds of the present invention.

Capping of failure sequences is carried out using a phosphodiester PEG moiety. Finally, in the oxidation step, the newly formed phosphite group of the growing oligonucleotide is converted to a phosphate group, for example, by reaction with aqueous iodine and pyridine. The four-step process may then be reiterated, since the oligonucleotide obtained after oxidation remains 5'-protected and is ready for use in the first deprotection step described above. When the desired oligonucleotide is obtained, it may be cleaved from the solid support, for example, by treatment with alkali and heat. This step may also serve to convert phosphate triesters to the phosphate diesters, as well as deprotect base-labile protected amino groups of the nucleotide bases.

Figure 11:
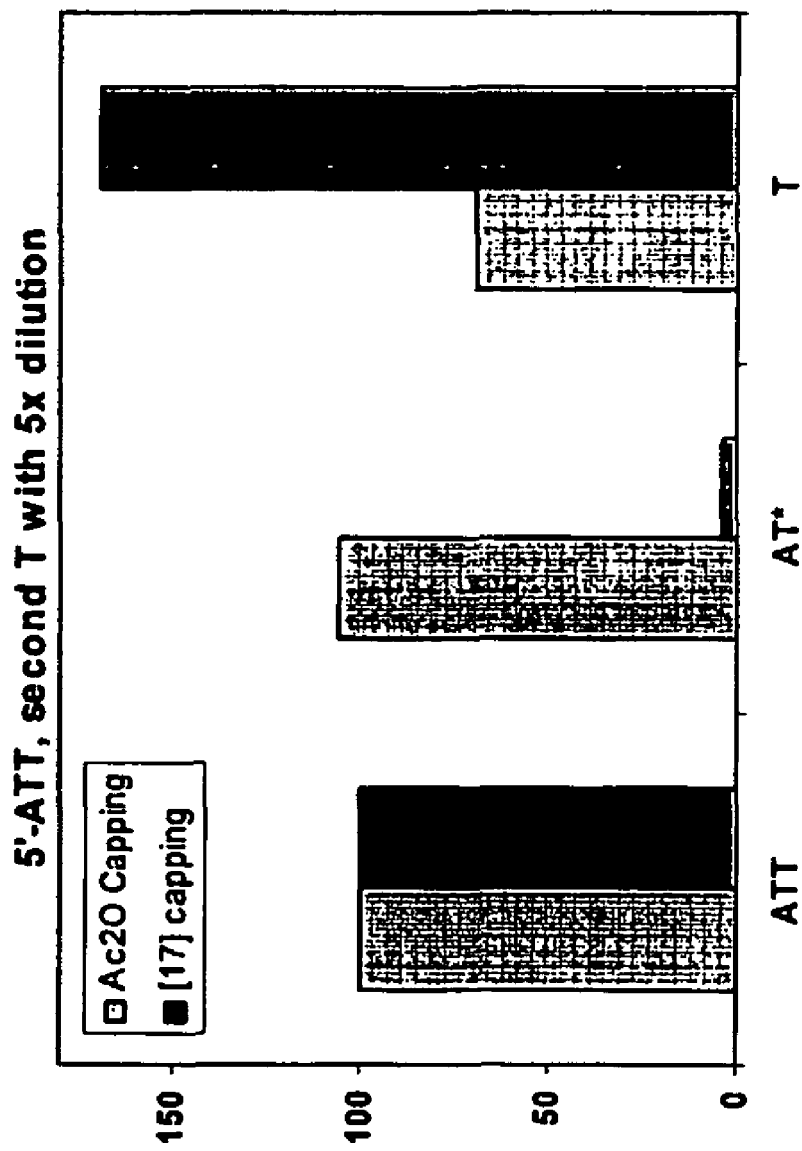
FIG. 11 illustrates the results of capping efficiency measured by the height of T (in the reaction of Ac2O capping or capped-T (in the reaction of [17] capping), for synthesis of 5'-ATT. The second step reaction for coupling T used diluted T phosphoramidite (dilution factor=5). [17] denotes diethylene glycol monoethyl ether phosphoramidite.
Figure 13:
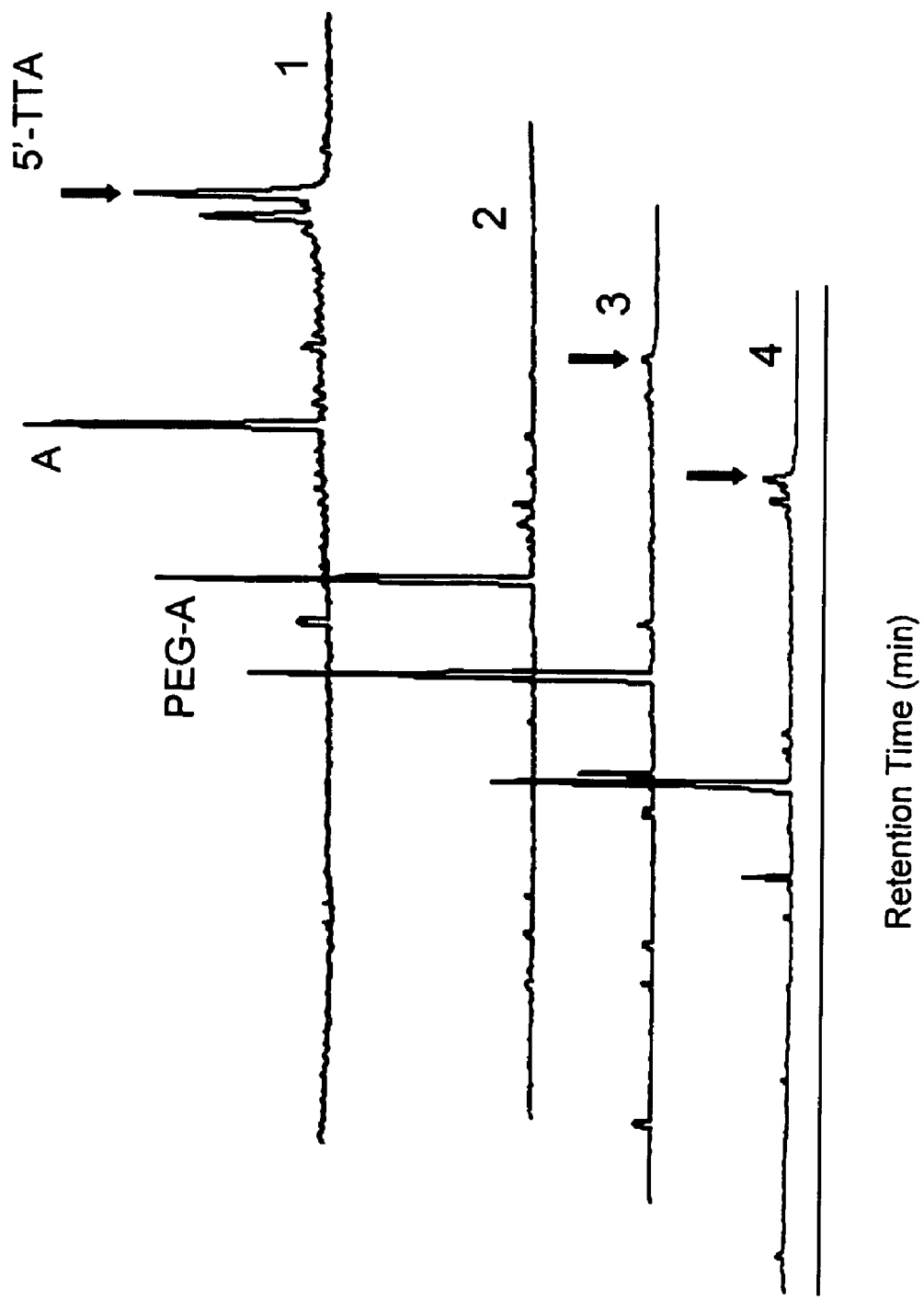
FIG. 13 illustrates the results of electrophoresis analysis of four reactions of 5'-TTA on CPG, all began with Ac2O capping on all reactive sites. Reaction 1 used regular synthesis conditions; reaction 2 used diethylene glycol monoethyl ether phosphoramidite five times and then at each capping step also used diethylene glycol monoethyl ether phosphoramidite; reaction 3 used diethylene glycol monoethyl ether phosphoramidite one time and then the same as reaction 2; reaction 4 used diethylene glycol monoethyl ether phosphoramidite one time and then used each capping step used Ac2O.

As shown in FIGS. 11 and 12, the capping efficiency of the compound of Formula I, where $R_1$ is —$CH_2CH_2CN$, $R_2$ is $(CH_2CH_2O)_n$—$OR_4$, $R_3$ is isopropyl, $R_4$ is Ethyl and n=2, is compared with that of regular capping using acetic anhydride (acetyl capping). Inefficient capping resulted in the continued growth of longer sequences but efficient coupling resulted in terminated sequences at the corresponding step. The capped sequences and the uncapped and thus longer sequences were well resolved on a reverse phase HPLC column; thus the capping efficiencies of the two reagents were easily compared. This comparison was especially evident when the coupling of the phosphoramidite was low (i.e. experiments deliberately designed to give low efficiency coupling to expose more unreacted sites). As depicted in FIGS. 11-13, the compound of the general Formula I is highly reactive and quantitative in terminating the reaction sites, while the conventional capping agent, acetic anhydrite, terminates only ~30% of the reaction sites.

Furthermore, oligonucleotides synthesized on controlled porous glass using either AC or PEG capping at the first step of the synthesis or at each reaction cycle, were analyzed by capillary electrophoresis (CE). As depicted in FIG. 13, capping with PEG reagents of the present invention gave a cleaner product sequence than capping using AC.

Compounds of the present invention are of the same type of compound as the phosphoramidite nucleotide monomers. Thus the capping reaction can be carried out immediately after the coupling step without the need for solvent washing between the two reaction steps. The use of the capping reagents of the present invention therefore reduces the overall reaction time compared to that using acetic acid anhydride.

As described above, the growing oligonucleotide may be attached to a support during synthesis. The support can be a solid or a soluble polymer, glass, silica, gold, metal oxide, or other suitable materials for chemical reactions. In one embodiment, the oligonucleotides are synthesized on solid support such as controlled porous glass (CPG).

The present invention also includes a method of modifying the properties of a surface to prevent non-specific binding in an assay. In one embodiment, a method is provided for preventing non-specific bonding of a molecule to reactive groups on a support by reacting a compound of Formula I or Formula II with the reactive groups on the support.

The compounds of Formula I and Formula II as described herein, are useful as surface property modifiers. As used herein, a modifier means a compound that reacts with reactive groups of a reactant compound to form a product that has different chemical properties from the reactant compound before its reaction with modifier. For instance, assays involving the binding of proteins or nucleic acids to probes on solid surfaces, such as those used in DNA or protein microarray applications, require non-adhesive surfaces so that binding occurs only where there are specific interactions. These assays normally detect binding or interactions by labeling the detection signals for example via fluorescent dye, of solution samples applied to a solid surface containing specific probes at specific locations. A good surface property is a surface which repels the binding of molecules so that the signal at the surface areas is very weak. A high contrast ratio of background signal and binding signal allows sensitive detection of weak signals.

PEG has favorable properties as a protein repellant. Compounds of the present invention allow effective termination of surface reactive groups such as OH or $NH_2$, while at the same time, place PEG chains onto the reacted surface. The density of PEG is controlled using a mixture of PEG capping and non-PEG capping reagents. The lengths of the PEG used in the surface capping reactions do not have to be similar or identical. Surface capping using PEGs of different lengths is achieved using a mixture of the PEG capping reagents having different n's in Formula I and Formula II.

The PEG modification can be used to direct desired changes in surface properties, such as hydrophilicity and hydrophobicity, to increase the aqueous biphasic alignment of the surface molecules.

The present invention also includes a method of modifying the properties of a molecule by reacting the molecule with a compound of Formula I or Formula II.

In one embodiment of the invention, Formula II depicts a monomer unit for synthesis of PEG-containing oligonucleotides or PEG grafted oligonucleotide conjugates, as shown above. The PEG-containing components can be incorporated into oligonucleotides in a controlled manner by using a mixture of reagents that include the compounds of the present invention and other compounds that can react with the surface reactive groups and also contain reactive group which is properly protected. The incorporation of the amount of the PEG-containing components into the oligonucleotides synthesized can thus be controlled by the ratio of the mixture reagents used. For example, a certain number of the PEG-containing components can be incorporated at certain positions to significantly change the properties of the PEG grafted oligonucleotide conjugates due to the special amphiphillic properties of PEG as discussed above. The method of incorporation is well known to those skilled in the art such as phosphoramidite chemistry using nucleotide monomers illustrated in FIGS. 5 and 7. The amphiphilic properties of these modified oligonucleotides should allow for improved formulation and delivery of oligonucleotides as drug molecules. (Choi, Y. H., Liu, F., Kim, J. S., Choi, Y. K., Park, J. S., Kim, S. W. (1998) Polyethylene glycol-grafted poly-L-lysine as polymeric gene carrier. J. Control Release. 54, 39-48). In addition, the modified oligonucleotides should show improved in vivo exonuclease stability, thermal stability, intermolecular interaction kinetics, and solution conformation. These properties may be adjusted or varied by the length of the PEG-containing segments incorporated into the grafted PEG-oligonucleotide conjugates.

The present invention also encompasses a method of controlling the density of reactive groups on a support by providing a predetermined amount of compounds of Formula I or Formula II and reacting such compounds with the reactive groups to obtain a desired density. For example, to control the density of reactive sites, the compounds of the present invention can be mixed with nucleotide phosphoramides which contain protected reactive groups in a predetermined ratio. The ratio can range from 1:2 to 1:10. The mixed phosphoramidites are then allowed to react with surface OH, NH2, carboxylate ester or other nucleophic groups. Once reacted with the compounds of the present invention, the reactive groups are no longer available for subsequent reactions. Thus after deprotection of nucleotides, the density of reactive groups are effectively reduced in a controlled manner.

The present invention further encompasses an oligomer synthesized by any method employing the compounds of Formula I or Formula II. For example, synthesis of oligomers may employ the compounds of the present invention as one or all of the following: capping reagents, or density controllers or surface property modifiers.

The present invention includes biological chips or microarrays or miniaturized detection devices comprising an oligomer synthesized by a method employing the compounds of Formula I and Formula II.

Biochip techniques can be employed in numerous applications such as identification/discovery of new genes and proteins, drug discovery, pharmacological and toxicological research, diagnosis, etc.

A microarray is a biochip product with an ordered arrangement of biological molecules immobilized in sample spots on a test plate which provides a medium for matching known and unknown samples of biological molecules. The immobilized molecules on the test plate are often denoted probe molecules, while the biological molecules from the test samples are denoted target molecules. In the case when the probe molecules and target molecules form specific complementary pairs of biological molecules, the ordered arrangement of the test spots can be employed to identify specific biological molecules in a test sample from an organism and determine the abundance of these molecules. Examples of biological molecules include nucleic acids and peptides. Microarrays may also be employed for comparison studies of biological components from several sources. For instance, biological components from a healthy cell and a tumor cell may be adsorbed onto the same array. DNA-microarray can monitor the whole genome on a single chip, and thereby make it possible to acquire a picture of the interactions between thousands of genes simultaneously. Microarrays are also useful in a variety of screening techniques for obtaining information about either the probes or the target molecules. For example, a library of peptides can be used as probes to screen for drugs. The peptides can be exposed to a receptor, and those probes that bind to the receptor can be identified. Microarrays are useful in diagnostic screening for genetic diseases or for the presence and/or identity of a particular pathogen or a strain of pathogen.

Microarray technology combines parallel synthesis or robotic placement (spotting) of small amounts of individual probes on a glass slide, intermolecular interactions of solution molecules with probes on a surface such as hybridization to this array with multiple fluorescently labeled target, and detection and quantitation of the resulting fluor-tagged hybrids with a scanning confocal fluorescent microscope. When used to detect transcripts, a particular RNA transcript (an mRNA) is copied into DNA (a cDNA) and this copied form of the transcript is immobilized on a glass slide. The entire complement of transcript mRNAs present in a particular cell type is extracted from cells and then a fluor-tagged cDNA representation of the extracted mRNAs is made in vitro by an enzymatic reaction termed reverse transcription. Fluor-tagged representations of mRNA from several cell types, each tagged with a fluor emitting a different color light, are hybridized to the array of cDNAs and then fluorescence at the site of each immobilized cDNA is quantitated.

Methods for producing arrays have been described in Hacia, J. G., Brody, L. C. & Collins, F. S., "Applications of DNA chips for genomic analysis", Mol. Psychiatry 3: 483-92, 1998; and Southern, E. M., "DNA chips: Analyzing sequence by hybridization to oligonucleotides on a large scale", Trends in Genetics 12:110-5, 1996, which are incorporated herein by reference.

EXAMPLES

Example 1

Synthesis of Diethylene Glycol Monoethyl Ether Phosphoramidite

Figure 10:
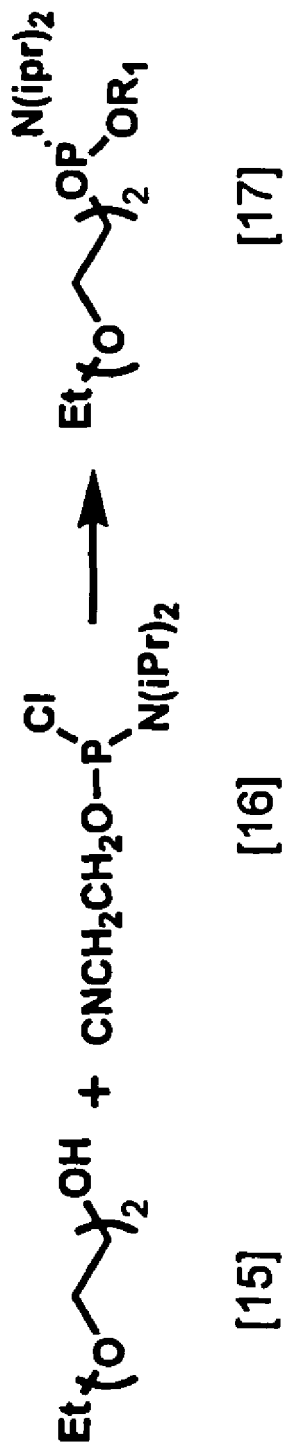
FIG. 10 depicts the synthesis of diethylene glycol monoethyl ether phosphoramidite.

The reaction is depicted in FIG. 10. The diethylene glycol monoethyl ether and 2-cyanoethyl-N,N,-diisopropylchlorophosphoramidite were purchased from Aldrich. $CH_2Cl_2$ was distilled from $CaH_2$; triethyl amine (TEA) was distilled from KOH. Chromatographic purification was carried out using silica gel 60 230-400 mesh (EM Separation Technology). A mixture solution of 10% $H_2SO_4$ (800 mL), $(NH_4)_6Mo_7O_{24}.6H_2O$ (40 g) and $Ce(SO_4)_2$ (0.8 g) was used for TLC detection. HPLC analysis was performed on a Waters 515 HPLC pump system equipped with a 2996 photodiode array detector using Waters' Empower software. The HPLC column used was RP-C18 8×10 10 µm µ-bondaPak) using a gradient solvent system (A: 0.05M triethylammonium acetate (TEAA) buffer pH ~6.5 containing 1% $CH_3CN$, B: $CH_3CN$). DNA synthesis reagents were purchased from Glen Research and EM Separation Technology. Controlled porous glass (CPG) used as the support for oligonucleotide synthesis was purchased from CPG Inc. Synthesis was performed on a 0.2 µmol scale using a DNA synthesizer (Expedite 8909, PerSeptive) and standard or modified protocols of phosphoramidite chemistry. NMR spectra were recorded on QE 300 MHz or AMX-II 600 MHz spectrometers (the University of Houston). $^{31}P$ chemical shift reference is external trimethylphosphate in a 0.1 M NaCl aq. solution (−4.0 ppm at 25° C.).

To a solution of diethylene glycol monoethyl ether (134 mg, 1 mmol) in anhydrous $CH_2Cl_2$ (6 mL) was added TEA (0.56 mL, 4 eq) followed by 2-cyanoethyl-N,N,-diisopropylchlorophosphoramidite (0.33 mL, 1.5 eq) drop-wise at room temperature under $N_2$ with stirring. The reaction was complete in about 1 hour. The reaction mixture was then cooled in an ice bath and TEA (1 mL) was added followed by addition of sat. $NaHCO_3$-ice $H_2O$ (~1:1, 5 mL) to quench the reaction. The reaction mixture was extracted with $CH_2Cl_2$, washed with brine once, dried over $Na_2SO_4$, and evaporated to dryness. The residue was purified on a short silica gel column (6 mL), using ethyl acetate:hexanes:TEA (2:3:0.05) as eluant, dried by high vacuo overnight, to afford diethylene glycol monoethyl ether phosphoramidite (250 mg) in 86% yield. NMR (600 MHz, $CDCl_3$, 295 K) δ (ppm): $^1H$ 1.17 (m, $CH_3$), 2.65 ($CH_2CN$), 3.52-3.84 (m, $CH_2$); $^{31}P$ 146.159.

Example 2

Comparison of Capping Efficiency of Phosphoramidous Acid, bis(1-methylethyl)-, 2-cyanoethyl 2-ethoxy-ethyl and $Ac_2O$ Synthesis of DNA oligonucleotide sequences was performed on a DNA synthesizer using CPG-T (0.2 µmol scale)

and DMT phosphoramidite chemistry. AT and ATT were synthesized by standard protocol. AT and ATT have absorbance maximum at 261.7 and 262.9 nm, respectively. These sequences were used as references for HPLC analysis.

(a) Comparison of the capping efficiency for the reactions using phosphoramidous acid, bis(1-methylethyl)-, 2-cyanoethyl 2-ethoxy-ethyl or acetic anhydride ($Ac_2O$) under the reaction condition where T phosphoramidite at a concentration lower than that for regular synthesis. The sequences synthesized were ATT and TTTT. In these syntheses, the three concentrations of the T phosphoramidite were diluted 5 or 10 times more than the regular concentration (50 mM). phosphoramidous acid, bis(I-methylethyl)-, 2-cyanoethyl 2-ethoxy-ethyl (30 mg) used was in anhydrous $CH_3CN$ (1 mL) and filtered by syringe filter (0.45 μm) before reaction. In the synthesis, the diluted T phosphoramidite was coupled with T on support CPG. The next reaction was either the regular $Ac_2O$ capping step [Cap Mix A: $THF/Ac_2O$ (9:1) and Cap Mix B: 10% MeIm in THF/pyridine (8:1)] or immediately in the same reaction cycle followed by reaction with phosphoramidous acid, bis(1-methylethyl)-, 2-cyanoethyl 2-ethoxy-ethyl without the regular capping step. After washing and oxidation steps as in a regular DNA synthesis, the surface sequences were coupled with an A phosphoramidite to afford ApTT, where p indicates the capping step using either $Ac_2O$ or phosphoramidous acid, bis(1-methylethyl)-, 2-cyanoethyl 2-ethoxy-ethyl. The sequences synthesized were deprotected and cleaved from the solid support in conc. $NH_4OH$ at 55° C. overnight. The supernatants of the reaction were dried on a lyophilizer. HPLC results of the synthesis using dilutions of 5 or 10 times and either $Ac_2O$ or phosphoramidous acid, bis(1-methylethyl)-, 2-cyanoethyl 2-ethoxy-ethyl capping are shown in FIG. 11 and FIG. 12. The detection of the monomer T (or 5'-phosphodiester capped T in phosphoramidous acid, bis(1-methylethyl)-, 2-cyanoethyl 2-ethoxy-ethyl capping since the capping group cannot be cleaved by $NH_4OH$ in the last step deprotection) is reversely proportional to the efficiency of capping. More complete capping results in a higher amount of the monomer T. In comparison, phosphoramidous acid, bis(1-methylethyl)-, 2-cyanoethyl 2-ethoxy-ethyl capping resulted in a much higher amount of monomer T. The detection of AT is due to the coupling of A with the uncapped T and AT was nearly absent in the phosphoramidous acid, bis(1-methylethyl)-, 2-cyanoethyl 2-ethoxy-ethyl capping but has significant presence in the $Ac_2O$ capping. This dramatic comparison also demonstrates much more efficient capping when using phosphoramidous acid, bis(1-methylethyl)-, 2-cyanoethyl 2-ethoxy-ethyl as the capping reagent. In these capillary electrophoresis plots, the peak at most right corresponding to 5'-TTA synthesized. The reactions were designed as such that if the capping is complete, there is no presence of 5'-TTA but only the capping product. The detection of 5'-TTA and its amount which is proportional to the peak height is due to inefficient capping and the degree of failure in capping (FIG. 13, reactions 2-5). For instance, the synthesis used performed using standard (FIG. 13, reaction 1) contained significant amount of failure sequences shown as addition peaks to the 5'-TTA. The synthesis used ten times of capping with [17] (FIG. 13, reaction 2) produced only capping product (PEG-A) and no further product after capping. LC-MS (positive mode, ESI, ideal mobile phase 10% $CH_3CN$ and 90% $H_2O$) m/z calculated for $C_{16}H_{27}N_2O_{10}P$ (PT) 438, found 439.3 ($M^+$ H)$^+$ and 461.3 ($M^+$ Na)$^+$; m/z calculated for $C_{30}H_{39}N_9O_{17}P_2$ (ATT) 859, found 860.1 ($M^+$ H)$^+$.

(b) This experiment describes the synthesis of 5'-TTA on CPG-A. The synthesis was performed on a DNA synthesizer using reagents and solvents as in regular DNA synthesis except for the capping step which used regular conditions or phosphoramidous acid, bis(1-methylethyl)-, 2-cyanoethyl 2-ethoxy-ethyl in anhydrous $CH_3CN$. The synthesis began with the step of capping using either $Ac_2O$ or phosphoramidous acid, bis(1-methylethyl)-, 2-cyanoethyl 2-ethoxy-ethyl and the HPLC results are shown in FIG. 4. The initial capping was to terminate the 5'-OH of CPG-A. If capping is efficient, there should be no further synthesis of any sequence. HPLC profile 1, shown in FIG. 13, is from a reaction using $Ac_2O$ capping at all steps and depicts a significant amount of the full length sequence 5'-TTA. HPLC profile 2 are results from phosphoramidous acid, bis(1-methylethyl)-, 2-cyanoethyl 2-ethoxy-ethyl capping and show no presence of 5'-TTA. HPLC profile 3 is from a synthesis where first step capping uses phosphoramidous acid, bis(1-methylethyl)-, 2-cyanoethyl 2-ethoxy-ethyl which is repeated five times and the rest of the synthesis uses $AC_2O$ capping, showing essentially no presence of 5'-TTA. HPLC profile 4 is from the synthesis where first step capping used phosphoramidous acid, bis(1-methylethyl)-, 2-cyanoethyl 2-ethoxy-ethyl and rest of the synthesis uses $AC_2O$ capping and shows a trace amount of 5'-TTA. These results unambiguously demonstrate phosphoramidous acid, bis(1-methylethyl)-, 2-cyanoethyl 2-ethoxy-ethyl is a highly efficient capping reagent compared to $AC_2O$ used in regular DNA synthesis.

Example 3

Oligonucleotide Synthesis

Oligonucleotides (PF1 and AF1) of 45-mers and identical sequences (5'-CTTTAAAATCAATACCTTTTAACTGAT-TCTATTAACAAGGGTATC) were synthesized. PF1 is referred as 5'-FAM-GFP10-compRev 2-PEGcapping and AF1 as 5'-FAM-GFP10-compRev 2-ACcapping.

The synthesis used Expertide 8909 DNA synthesizer and 0.2 μmol standard protocol and was performed on a CPG support. The deprotection at each synthesis cycle used either acetyl capping solutions from Glen Research (AC capping) or the diethylene glycol monoethyl ether phosphoramidite (EDEGP for PEG capping) (having the structure shown below) in $CH_3CN$ (90 mM).

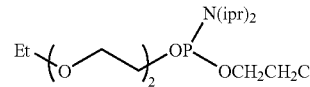

The PEG capping step followed immediately after the coupling of nucleophosphoramidites and used 0.075 mL delivered at default rate of flow. The PEG capping reagent was activated using tetrazole in CH3CN (0.45 M, Glen Research), which is also the activator for nucleophosphoramidite coupling reaction. The rest of the synthesis was identical to that of the AC capping synthesis. The oligonucleotides were deprotected in concentrated aqueous ammonia (0.5 mL) at 55° C. for 16 h.

Example 4

Nuclease Enzyme Digestion of Oligonucleotides

Figure 14:
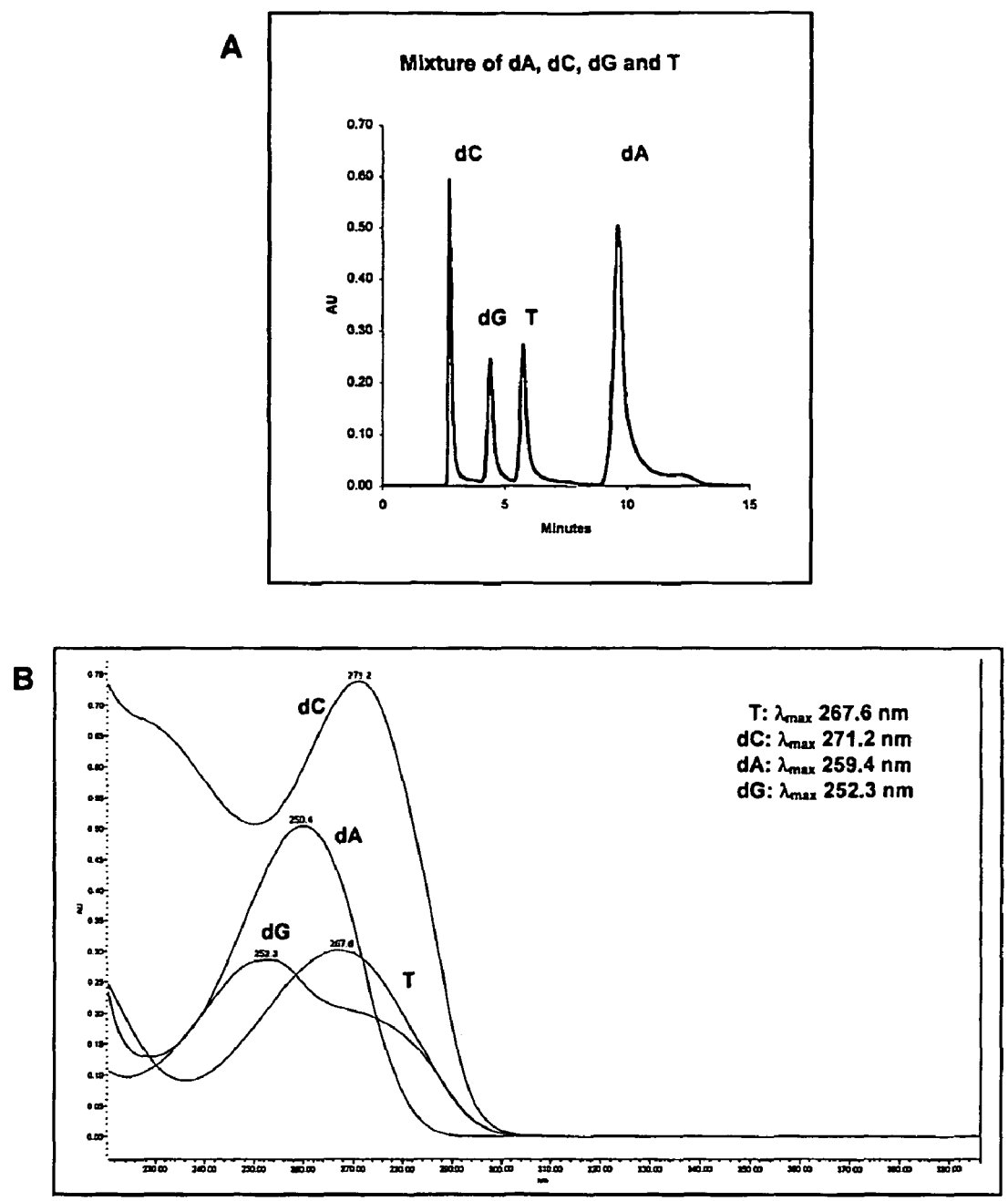
FIG. 14 illustrates HPLC (A) and UV (B) profiles of the nucleosides from commercial source (ChemGenes) recorded using a photodiode array detector on a Waters system.
Figure 15:
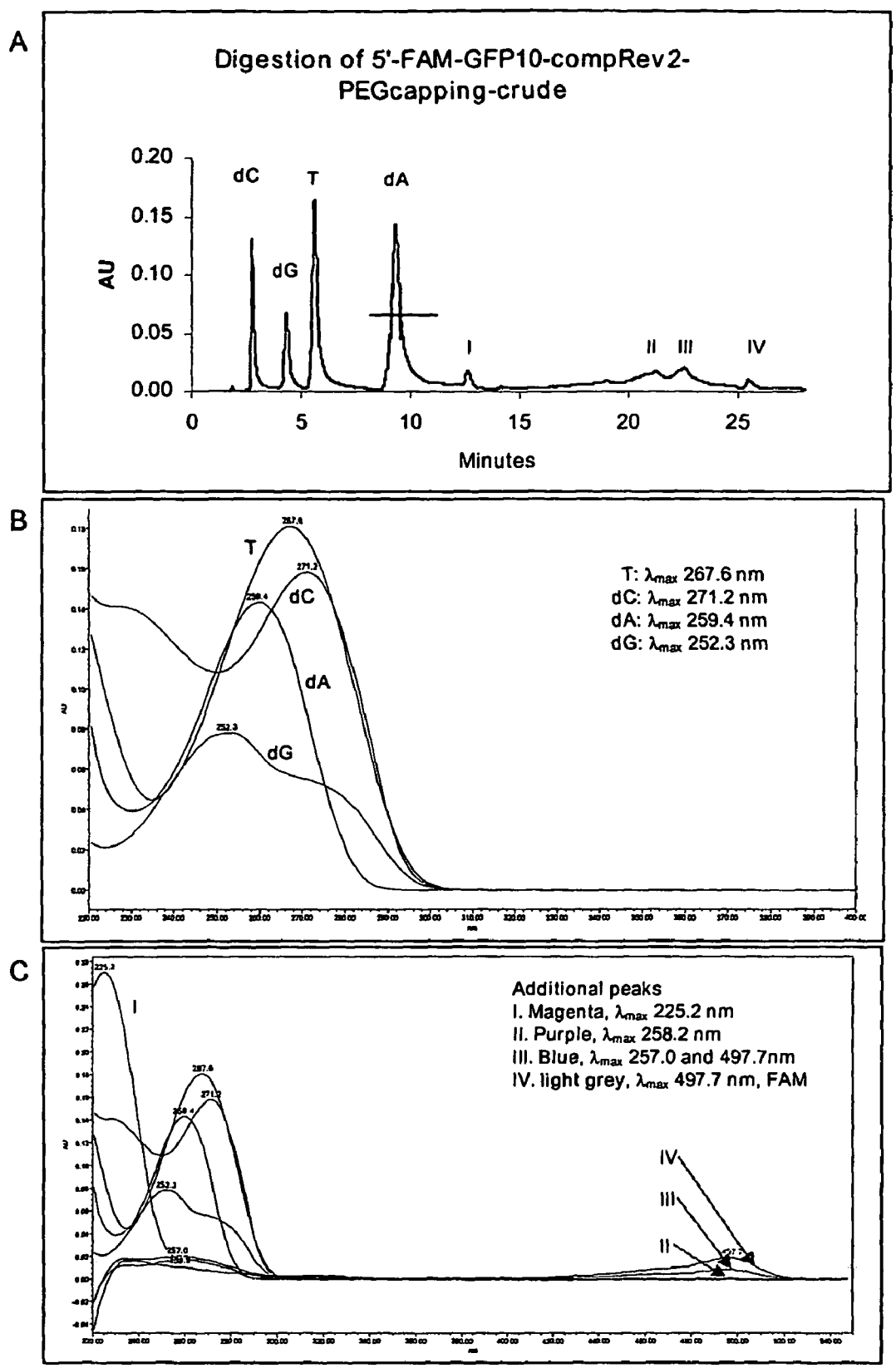
FIG. 15 illustrates HPLC (A) and UV (B and C) profiles of the nucleosides obtained after enzymatic digestion of 5'-CTT-TAAAATCAATACCTTTTAACTGATTC-TATTAACAAGGGTATC synthesized using diethylene glycol monoethyl ether phosphoramidite capping recorded using a photodiode array detector on a Waters system.
Figure 16:
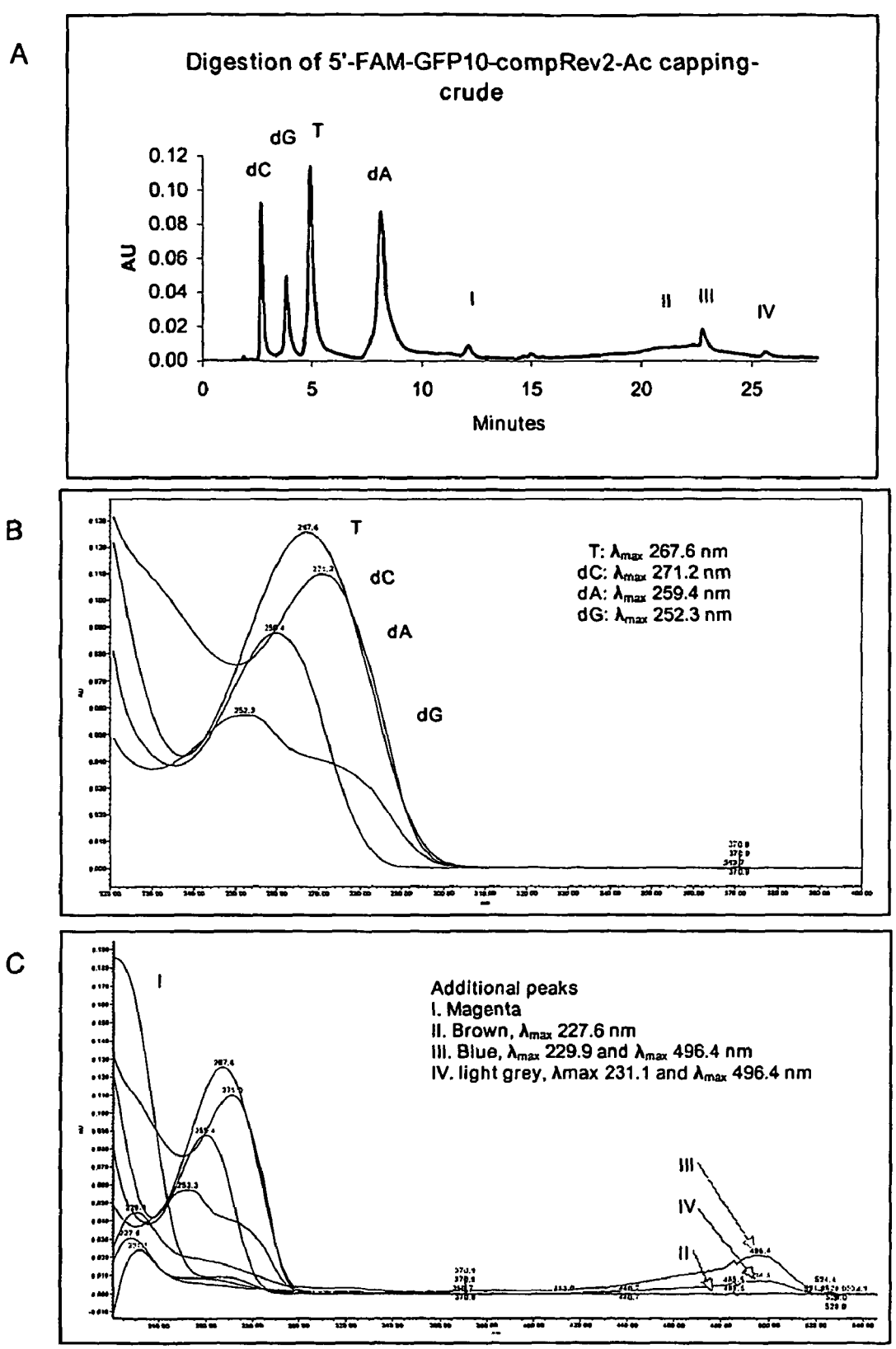
FIG. 16 illustrates HPLC (A) and UV (B and C) profiles of the nucleoside obtained after enzymatic digestion of 5'-CTT-TAAAATCAATACCTTTTAACTGATTC-TATTAACAAGGGTATC synthesized using $Ac_2O$ capping recorded using a photodiode array detector on Waters system.

Enzymatic digestion was performed using phosphodiesterase 1 (PDE 1, *Crotalus adamanteus* Venom) (Worthington-Biochem) in which the stock solution is 129 u/mL and alkaline phosphatase (Calf Intestinal), or CIAP (Promega) in which the stock solution is 20 u/μL. PDE 1 was diluted to 0.01 u/μL in 1×PDE 1 buffer (0.11 M tris-HCl, 0.11 M NaCl, 15 mM $MgCl_2$, pH 8.9) of total 12.9 μL. CIAP was diluted to 1 u/μL in 1×CIAP buffer (50 mM Tris-HCl, 1 mM $MgCl_2$, 0.1 mM $ZnCl_2$, and 1 mM spermidine, pH 9.3) of total 10 μL. 1 OD (UV 260 nm) of oligonucleotide was dissolved in 1×PDE 1 buffer (90 μL) and mixed with PDE 1 (0.01 u/μL, 10 μL). The sample was incubated at rt for 2 h to give 5'dNMP. To this sample dd$H_2O$ (801 μL) was added and then CIAP (1 u/μL, 10 μL) in CIAP 10× reaction buffer (89 μL) were added. The reaction mixture was and incubated at 37° C. for 1.5 h to give 2'-deoxynucleosides. The reaction mixture was cooled and neutralized with 1 N HCl and H2O was removed by spinning-drying. The comparison of the standard nucleosides and those obtained from enzyme digestion reactions are shown in FIGS. 14-16.

Validating Oligonucleotide Synthesis Using Enzymatic Digestion

For the enzymatic digestion of 45-mer oligonucleotides of the sequence, 5'-CTTTAAAATCAATACCTTTTAACTGAT-TCTATTAACAAGGGTATC, using AC or PEG capping, the PEG agent was used following the addition of nucleophosphoramidite after each coupling step without requiring additional solvents for the reaction. As shown in FIGS. 14-16, the UV profiles obtained from HPLC photodiode array detector of the enzymatic digestion product nucleosides are shown identical to the reference nucleosides and those from the AC capping sequence. A minor population of undigested residual oligonucleotide is detectable at Peaks II and III in FIG. 15. The presence of modified nucleosides is negligible.

Example 5

HPLC Analysis

The full length oligonucleotides and the reaction mixture of the enzymatic digestion of the crude products of oligonucleotide synthesis were analyzed using reverse phase HPLC equipped with photodiode array detector. These results are shown in FIG. 15 and FIG. 16. FIG. 14 shows HPLC data of four standard nucleosides.

Predicated ratio: dC:dG:T:dA=4.0:2.0:1.0:4.3; experimental ratio=4.2:2.0:1.0:4.0

Example 6

MASS Analysis

The oligonucleotides synthesized were analyzed (Applied Biosystems Voyager System 4160, MALDI-TOF positive mode, calibration matrix: 3-hydroxypicolinic acid): 14,286.5. Calc. FAM-CTTTAAAATCAATACCTTT-TAACTGATTCTATTAACAAGGGTATC 14,288.5.

Example 7

Oligonucleotide Microarry Synthesis on Biochip

An oligonucleotide microarray containing 3888 sequences, which are selected from human cancer related genes, were synthesized as described previously (Gao et al. (2001) Flexible DNA chip synthesis gated by deprotection using solution photogenerated acids. *Nucleic Acids Res.* 29, 4744-4750), incorporated herein by reference. One chip synthesis used regular protocol with AC capping and the other chip used the same protocol except for the PEG capping as described above for the oligonucleotide synthesis on CPG.

Example 8

DNA Chip Hybridization Using cDNA Samples

Two cDNA samples were prepared according to procedures as described in DNA Microarrays and Gene Expression: From Experiments to Data Analysis and Modeling by Pierre Baldi, G. Wesley Hatfield, Wesley G. Hatfield. Cambridge, UK.

Figure 17:
FIG. 17 illustrates DNA chip hybridization images. cDNA samples were used to hybridize with oligonucleotide probes on chip. Oligonucleotides synthesized on chip using (A) Ac$_2$O in the capping step, or (B) diethylene glycol monoethyl ether phosphoramidite in the capping step.
Figure 17:
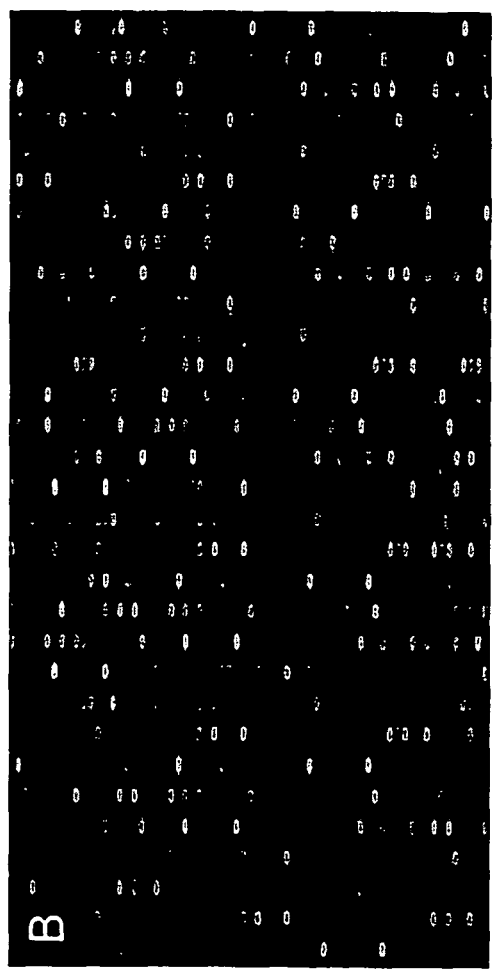

The universal (univ) and skeletal muscel (sk) total RNA was from CloneTech. Florescence cy3 and cy5 dyes were incorporated using dye-dU for the univ and sk cDNA samples, respectively. The co-hybridization of the cDNA samples to the DNA chip used 6×SSPE (0.9 M NaCl, 60 mM $Na_2HPO_4$, 6 mM EDTA, pH 6.8) buffer (80 μL) mixed with 25% formamide at 32° C. for 18 h under micro-flow conditions. The chips were washed briefly with the 6×SSPE buffer before image scanning on an Axon GenePix 4000B laser scanner. The PMT level was adjusted according the signal strength observed. The images of the AC capping and PEG capping DNA chips are shown in FIG. 17.

Example 9

Validating Oligonucleotide Synthesis on Chip Using Hybridization

The PEG capping was implemented in DNA chip synthesis and the comparison chip was synthesized using regular AC capping. These experiments were to compare hybridization results when the two DNA chips were treated with cDNA samples labeled with cy3 (universal total RNA sample) or cy5 (skeletal muscle total RNA sample) fluorescent dye. The two samples were co-hybridized to chip and ratio of cy3 to cy5 is shown in color ranging from green (cy3>cy5) to yellow (cy3=cy5) to red (cy5>cy3). The color ratio image comparison of the PEG capping versus the AC capping chip (FIG. 17) shows highly comparable results. This result validates PEG capping is applicable to DNA microarray synthesis for the improvement of capping efficiency, which is critical for the initial synthesis steps of in situ oligonucleotide synthesis on glass surfaces. The capping reaction time using the PEG capping reagent is several folds shorter than that of AC capping.

Detailed embodiments of the present invention are disclosed herein. However, it is to be understood that the disclosed embodiments are merely exemplary of the invention that may be embodied in various and alternative forms. The figures are not necessarily to scale where some features may be exaggerated or minimized to show details of particular components. Therefore, specific structural and functional details disclosed herein are not to be interpreted as limiting, but merely as a basis for the claims and as a representative basis for teaching one skilled in the art to variously employ the present invention.

Although making and using various embodiments of the present invention have been described in detail above, it should be appreciated that the present invention provides many applicable inventive concepts that can be embodied in a wide variety of specific contexts. The specific embodiments discussed herein are merely illustrative of specific ways to make and use the invention, and do not delimit the scope of the invention.

We claim:
1. A compound of the formula:

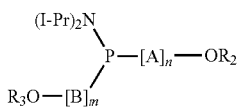

wherein
A is selected from the group consisting of —(OCH$_2$CH$_2$)—, —(OCH$_2$CH$_2$CH$_2$)—, and grafted —(OCH$_2$CH$_2$)$_{n1}$—(OCH$_2$CH$_2$CH$_2$)$_{n2}$—;
B is selected from the group consisting of —(OCH$_2$CH$_2$)—, —(OCH$_2$CH$_2$CH$_2$)—, and grafted —(OCH$_2$CH$_2$)$_{m1}$—(OCH$_2$CH$_2$CH$_2$)$_{m2}$—;
n is 1-50;
n1 is 1-50;
n2 is 1-50;
m is 1-50;
m1 is 1-50;
m2 is 1-50;
I—Pr is isopropyl;
R$_2$ is selected from the group consisting of H, —CH$_3$, alkyl, phenyl, —CH$_2$CH$_2$CN and CONH$_2$;
R$_3$ is selected from the group consisting of H, —CH$_3$, alkyl, phenyl, —CH$_2$CH$_2$CN and CONH$_2$.

2. The compound of claim 1 wherein A is —(OCH$_2$CH$_2$)—, B is —(OCH$_2$CH$_2$)—, n is 2, m is 2, R$_2$ is CH$_3$ or CH$_2$CH$_3$, and R$_3$ is CH$_3$ or CH$_2$CH$_3$.

3. The compound of claim 1 wherein A is —(OCH$_2$CH$_2$)—, B is —(OCH$_2$CH$_2$)—, n is 3-20, m is 3-20, R$_2$ is CH$_3$ or CH$_2$CH$_3$, and R$_3$ is CH$_3$ or CH$_2$CH$_3$.

* * * * *